US012766001B2

(12) United States Patent
Miller et al.

(10) Patent No.: US 12,766,001 B2
(45) Date of Patent: Oct. 20, 2026

(54) STEMLESS ORTHOPEDIC IMPLANTS WITH SENSORS

(71) Applicant: Biomet Manufacturing, LLC, Warsaw, IN (US)

(72) Inventors: Kevin Miller, Wakarusa (IN); Nathan A. Winslow, Scottsdale, AZ (US); Raymond C. Parisi, Wakarusa (IN); Andrew Scott Payton, Warsaw, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 579 days.

(21) Appl. No.: 18/217,819

(22) Filed: Jul. 3, 2023

(65) Prior Publication Data

US 2024/0008993 A1 Jan. 11, 2024

Related U.S. Application Data

(60) Provisional application No. 63/423,957, filed on Nov. 9, 2022, provisional application No. 63/359,492, filed on Jul. 8, 2022.

(51) Int. Cl.

| | |
|---|---|
| ***A61F 2/40*** | (2006.01) |
| ***A61F 2/30*** | (2006.01) |
| ***A61F 2/48*** | (2006.01) |

(52) U.S. Cl.

CPC ........ *A61F 2/4003* (2013.01); *A61F 2/30749* (2013.01); *A61F 2/482* (2021.08);

(Continued)

(58) Field of Classification Search

CPC .... A61F 2/4003; A61F 2/30749; A61F 2/482; A61F 2002/30332; A61F 2002/30606;

(Continued)

(56) References Cited

U.S. PATENT DOCUMENTS

| | | | |
|---|---|---|---|
| 6,245,109 | B1 | 6/2001 | Mendes et al. |
| 6,573,706 | B2 | 6/2003 | Mendes et al. |

(Continued)

FOREIGN PATENT DOCUMENTS

| | | |
|---|---|---|
| CN | 113951824 | 1/2022 |
| JP | 2005288172 | 10/2005 |

(Continued)

OTHER PUBLICATIONS

"International Application Serial No. PCT US2023 026846, International Search Report mailed Sep. 26, 2023", 5 pgs.

(Continued)

*Primary Examiner* — Bruce E Snow

(74) *Attorney, Agent, or Firm* — Schwegman Lundberg & Woessner, P.A.

(57) ABSTRACT

A humeral arthroplasty system includes a sensor device, a humeral head including a first portion of circuitry of the sensor device and an adapter socket, a taper adapter configured to seat within the adapter socket, a stemless humeral anchor couplable to the taper adapter, and a second portion of circuitry of the sensor device extending into the adapter socket. The taper adapter and the stemless humeral anchor can comprise a central bore extending therethrough, and the second portion of the circuitry of the sensor device can be connected to the first portion by an electrical circuit extending through the taper adapter. The humeral head can comprise a ceramic material. The second portion of circuitry can comprise a force sensor extending into the adapter socket, wherein the taper adapter is configured to engage the force sensor when seated in the adapter socket.

27 Claims, 14 Drawing Sheets

(52) U.S. Cl.
CPC ............... *A61F 2002/30332* (2013.01); *A61F 2002/30606* (2013.01); *A61F 2002/3067* (2013.01); *A61F 2002/4018* (2013.01)

(58) Field of Classification Search
CPC ...... A61F 2002/3067; A61F 2002/4018; A61F 2/4684; A61F 2002/30011; A61F 2002/30565; A61F 2/488; A61F 2002/3092; A61F 2002/3093; A61F 2/40; A61F 2002/40011; A61F 2/4014; A61B 5/0031; A61B 5/4576; A61B 5/4851
See application file for complete search history.

(56) References Cited

U.S. PATENT DOCUMENTS

| | | | |
|---|---|---|---|
| 6,706,005 | B2 | 3/2004 | Roy et al. |
| 6,821,299 | B2 | 11/2004 | Kirking et al. |
| 6,918,308 | B2 | 7/2005 | Biedermann et al. |
| 7,097,662 | B2 | 8/2006 | Evans, III et al. |
| 7,210,240 | B2 | 5/2007 | Townsend et al. |
| 7,256,695 | B2 | 8/2007 | Hamel et al. |
| 7,395,167 | B2 | 7/2008 | Frolik |
| 7,412,897 | B2 | 8/2008 | Crottet et al. |
| 7,470,288 | B2 | 12/2008 | Dietz et al. |
| 7,478,108 | B2 | 1/2009 | Townsend et al. |
| 7,575,602 | B2 | 8/2009 | Amirouche et al. |
| 7,578,821 | B2 | 8/2009 | Fisher et al. |
| 7,587,945 | B2 | 9/2009 | Crottet et al. |
| 7,672,781 | B2 | 3/2010 | Churchill et al. |
| 7,786,867 | B2 | 8/2010 | Hamel et al. |
| 7,831,403 | B2 | 11/2010 | Frolik |
| 7,842,092 | B2 | 11/2010 | Otto et al. |
| 7,918,887 | B2 | 4/2011 | Roche |
| 7,970,734 | B2 | 6/2011 | Townsend et al. |
| 8,029,566 | B2 | 10/2011 | Lozier et al. |
| 8,032,486 | B2 | 10/2011 | Townsend et al. |
| 8,065,927 | B2 | 11/2011 | Crottet et al. |
| 8,080,064 | B2 * | 12/2011 | Dietz ...................... A61F 2/389 623/20.32 |
| 8,197,549 | B2 | 6/2012 | Amirouche et al. |
| 8,506,638 | B2 | 8/2013 | Vanasse et al. |
| 8,884,618 | B2 | 11/2014 | Mahfouz |
| 8,956,418 | B2 | 2/2015 | Wasielewski et al. |
| 8,992,623 | B2 | 3/2015 | Hopkins et al. |
| 9,021,277 | B2 | 4/2015 | Shearer et al. |
| 9,248,020 | B2 | 2/2016 | Popoola et al. |
| 9,675,461 | B2 | 6/2017 | Mahfouz |
| 10,492,686 | B2 | 12/2019 | Hunter et al. |
| 10,966,788 | B2 | 4/2021 | Britton et al. |
| 2007/0005145 | A1 | 1/2007 | Banks et al. |
| 2007/0233267 | A1 | 10/2007 | Amirouche et al. |
| 2007/0234819 | A1 | 10/2007 | Amirouche et al. |
| 2007/0239165 | A1 | 10/2007 | Amirouche |
| 2008/0065225 | A1 | 3/2008 | Wasielewski et al. |
| 2009/0005708 | A1 | 1/2009 | Johanson et al. |
| 2009/0138019 | A1 | 5/2009 | Wasielewski |
| 2009/0287310 | A1 | 11/2009 | Fisher et al. |
| 2009/0299483 | A1 | 12/2009 | Amirouche et al. |
| 2010/0198275 | A1 | 8/2010 | Chana et al. |
| 2010/0217156 | A1 | 8/2010 | Fisher et al. |
| 2010/0249533 | A1 | 9/2010 | Pierce et al. |
| 2010/0249534 | A1 | 9/2010 | Pierce et al. |
| 2010/0249535 | A1 | 9/2010 | Pierce et al. |
| 2010/0249658 | A1 | 9/2010 | Sherman |
| 2010/0249659 | A1 | 9/2010 | Sherman et al. |
| 2010/0249660 | A1 | 9/2010 | Sherman et al. |
| 2010/0249777 | A1 | 9/2010 | Sherman et al. |
| 2010/0249789 | A1 | 9/2010 | Rock et al. |
| 2010/0249790 | A1 | 9/2010 | Roche |
| 2010/0250276 | A1 | 9/2010 | Pierce et al. |
| 2010/0326210 | A1 | 12/2010 | Stein et al. |
| 2010/0326211 | A1 | 12/2010 | Stein |
| 2010/0328077 | A1 | 12/2010 | Stein |
| 2010/0328098 | A1 | 12/2010 | Stein et al. |
| 2010/0331633 | A1 | 12/2010 | Stein |
| 2010/0331682 | A1 | 12/2010 | Stein et al. |
| 2010/0331683 | A1 | 12/2010 | Stein et al. |
| 2010/0331718 | A1 | 12/2010 | Stein |
| 2010/0331733 | A1 | 12/2010 | Stein |
| 2010/0331734 | A1 | 12/2010 | Stein |
| 2010/0331736 | A1 | 12/2010 | Stein |
| 2010/0331737 | A1 | 12/2010 | Stein et al. |
| 2010/0331894 | A1 | 12/2010 | Stein |
| 2010/0332152 | A1 | 12/2010 | Stein |
| 2011/0118566 | A1 | 5/2011 | Roche |
| 2011/0124981 | A1 | 5/2011 | Roche |
| 2011/0160616 | A1 | 6/2011 | Stein et al. |
| 2011/0160738 | A1 | 6/2011 | Mcintosh et al. |
| 2013/0018475 | A1 | 1/2013 | Vanasse et al. |
| 2013/0197656 | A1 | 8/2013 | Conrad |
| 2017/0312035 | A1 | 11/2017 | May et al. |
| 2018/0125365 | A1 | 5/2018 | Hunter et al. |
| 2018/0161168 | A1 | 6/2018 | Johannaber et al. |
| 2019/0159906 | A1 | 5/2019 | Knox et al. |
| 2019/0350518 | A1 | 11/2019 | Bailey et al. |
| 2020/0107945 | A1 | 4/2020 | Trousdale et al. |
| 2024/0325153 | A1 * | 10/2024 | Winslow ............... A61F 2/4059 |
| 2026/0007523 | A1 * | 1/2026 | Robicheaux .............. A61F 2/40 |

FOREIGN PATENT DOCUMENTS

| | | |
|---|---|---|
| JP | 2018530358 | 10/2018 |
| JP | 2025521923 | 7/2025 |
| WO | 2021257962 | 12/2021 |
| WO | 2024010766 | 1/2024 |

OTHER PUBLICATIONS

"International Application Serial No. PCT US2023 026846, Written Opinion mailed Sep. 26, 2023", 5 pgs.
"International Application Serial No. PCT US2023 026846, International Preliminary Report on Patentability mailed Jan. 23, 2025", 7 pgs.
"European Application Serial No. 23749202.0, Response Filed Aug. 12, 2025 to Communication pursuant to Rules 161(1) and 162 EPC mailed Feb. 18, 2025", 52 pgs.
"Australian Application Serial No. 2023304183, First Examination Report mailed Aug. 18, 2025", 4 pgs.
"Japanese Application Serial No. 2025-500232, Notification of Reasons for Refusal mailed Jan. 20, 2026", w English Translation, 11 pgs.
"Japanese Application Serial No. 2025-500232, Response filed Apr. 16, 2026 to Notification of Reasons for Refusal mailed Jan. 20, 2026", W/English Claims, 17 pgs.

* cited by examiner

STEMLESS ORTHOPEDIC IMPLANTS WITH SENSORS

CLAIM OF PRIORITY

This application claims the benefit of U.S. Provisional Patent Application Ser. No. 63/359,492, filed on Jul. 8, 2022, and claims the benefit of U.S. Provisional Patent Application Ser. No. 63/423,957, filed on Nov. 9, 2022, the benefit of priority of each of which is claimed hereby, and each of which is incorporated by reference herein in its entirety.

TECHNICAL FIELD

The present disclosure is generally directed to, but not by way of limitation, systems, devices and methods incorporating sensors for use in performing, monitoring and evaluating medical procedures, such as arthroplasty procedures. More specifically, but not by way of limitation, the present disclosure is directed to orthopedic and prosthetic implants that incorporate sensors.

BACKGROUND

Arthroplasty procedures involve the implantation of medical devices, e.g., orthopedic and prosthetic implants, into anatomy of a patient. Typically, once the medical device is implanted into the patient, or even while it is being implanted, it is difficult to obtain feedback regarding the effectiveness of the implant or the implant procedure. Attempts have been made to obtain data from orthopedic implants using sensors.

Pub. No. US 2018/0125365 to Hunter et al. is titled "Devices, Systems and Methods for Using and Monitoring Medical Devices."

Pub. No. US 2019/0350518 to Bailey et al. is titled "Implantable Reporting Processor for an Implant."

U.S. Pat. No. 10,492,686 to Hunter et al. is titled "Devices, Systems and Methods for Using and Monitoring Medical Devices."

OVERVIEW

The present inventors have recognized, among other things, that problems to be solved with conventional sensor systems used in conjunction with implantable medical devices, such as orthopedic prosthetic devices, involve the necessity to include sensor systems within the envelope of existing prosthetic device designs. For example, sensor systems include batteries and electronics that must be stowed within the implanted prosthetic device. The prosthetic device must, therefore, be not only be large enough to accommodate the battery and electronics, but the battery and electronics must fit within the form factor of the prosthetic device. Redesigning the prosthetic device to include the battery and electronics can increase in size of the prosthetic device, which can result in removal of excess bone from the patient to accommodate the larger prosthetic device.

The present inventors have further recognized that problems exist with incorporating electronics modules into stemless prosthetic devices. For example, many prosthetic devices utilize a stem that can be inserted into bone matter to immobilize the prosthetic device and facilitate attachment to bone. The stem can comprise an elongate body that can be inserted deep into cancellous bone matter, which can tightly hold the stem and thus the prosthetic device relative to the bone. The stem provides a body having a large volume into which electronic components can be mounted. However, the use of stems can sometimes be disadvantageous in that the stem can displace healthy cancellous bone and can sometimes form a structural risk to the cortical bone surrounding the cancellous bone. For example, driving of the stem, which can be made of hard material such as stainless steel, titanium alloy, or cobalt chrome, into the cancellous bone, sometimes with a hammer or mallet, can cause stress and fracturing of the cortical bone. Thus, it is desirable to use prosthetic devices that have stemless fixation. However, stemless fixation systems do not include components having large volumes that can be used to house electronics components or power sources. As such, the present inventors have recognized that many stemless anchored prosthetics desirably have small bone matter footprints to minimize impact to the anatomy, which simultaneously undesirably shrinks the available space on the prosthetic device to include electronics components.

The present inventors have yet further recognized that problems exist in transmitting data from embedded sensors out of the prosthetic device. Prosthetic orthopedic implants are typically largely metallic in construction, which makes transmitting wireless signals difficult or impossible. Accordingly, in addition to the problems discussed above, the following subject matter addresses the issue of data transmission through use of a multi-component sensor device.

The present inventors have also recognized that it can be difficult to intraoperatively determine if prosthetic orthopedic implants are properly mated together during assembly. It can be difficult to determine if prosthetic head components are properly mounted to anchor components. A surgeon may need to attach and remove multiple prosthetic head components intraoperatively to find the proper joint tension and the like. Each time, tissue and blood can interfere with performing the assembly and impede visibility. The present inventors have recognized that, due at least in part to the aforementioned lack of sensing capabilities in orthopedic implants, collecting intra-operative sensor data has been unavailable.

The present subject matter can provide solutions to these and other problems, such as by providing sensor-enabled orthopedic implants that can have electronics modules separated into different components connected by electrical leads, wherein each component can be positioned at a different part or location of the prosthetic device. Conventional sensor modules typically comprise a single housing, thereby requiring the prosthetic device to have a large space to accommodate the housing for the entire electronics module. With the present disclosure, the electronics module can be separated into different elements, such as battery, circuitry, antenna and the like. The different elements can be positioned in different locations of the prosthetic device, such as articulating component, adapter component, anchor component and the like. As such, various elements of the electronics module can be more advantageously positioned, such as by having sensor elements located closer to the desired sensing location and antenna elements located in positions amenable to transmitting wireless signals, such as further away from metallic components of the prosthetic device.

The present subject matter can provide solutions to these and other problems by providing prosthetic humeral head components that can be made of materials that facilitates transmission of electronic and wireless communication signals therethrough. For example, electronic signals, e.g., electrical current, can be communicated through conductive material, such as stainless steel, cobalt-chromium alloys, and titanium. In examples, wireless communication signals, e.g., radio waves, can be transmitted through non-blocking material such as ceramic. In examples, humeral head components can be made of composite or compound The present subject matter can provide solutions to these and other problems by providing prosthetic humeral head components that include sensors that can provide intraoperative and post operative feedback. In examples, such feedback can include force feedback, contact feedback, motion feedback and the like.

1) The present subject matter includes the use of sensor-enabled implantable prosthetic devices that can fit within the form factor of existing designs.
2) The present subject matter includes the use of sensor-enabled implantable prosthetic devices that can be used with stemless prosthetic devices that do not have a large amount of internal space for storing electronics modules.
3) The present subject matter includes the use of sensor-enabled implantable prosthetic devices that can allow for more advantageous locating of various electronic elements.
4) The present subject matter includes the use of prosthetic components fabricated from materials that facilitate transmission of electronic and wireless signals.
5) The present subject matter includes sensor-enabled implantable prosthetic devices that can provide feedback as to the coupling of various components of the prosthetic devices.

In an example, a humeral arthroplasty system includes a sensor device, a humeral head including a first portion of circuitry of the sensor device and an adapter socket, a taper adapter configured to seat within the adapter socket, a stemless humeral anchor couplable to the taper adapter, and a second portion of circuitry of the sensor device extending into the adapter socket. In another example, the taper adapter and the stemless humeral anchor can comprise a central bore extending therethrough, and the second portion of the circuitry of the sensor device can be connected to the first portion by an electrical circuit extending through the taper adapter. In another example, the humeral head can comprise a ceramic material. The second portion of circuitry can comprise a force sensor extending into the adapter socket, wherein the taper adapter is configured to engage the force sensor when seated in the adapter socket.

DETAILED DESCRIPTION

Figure 1A:
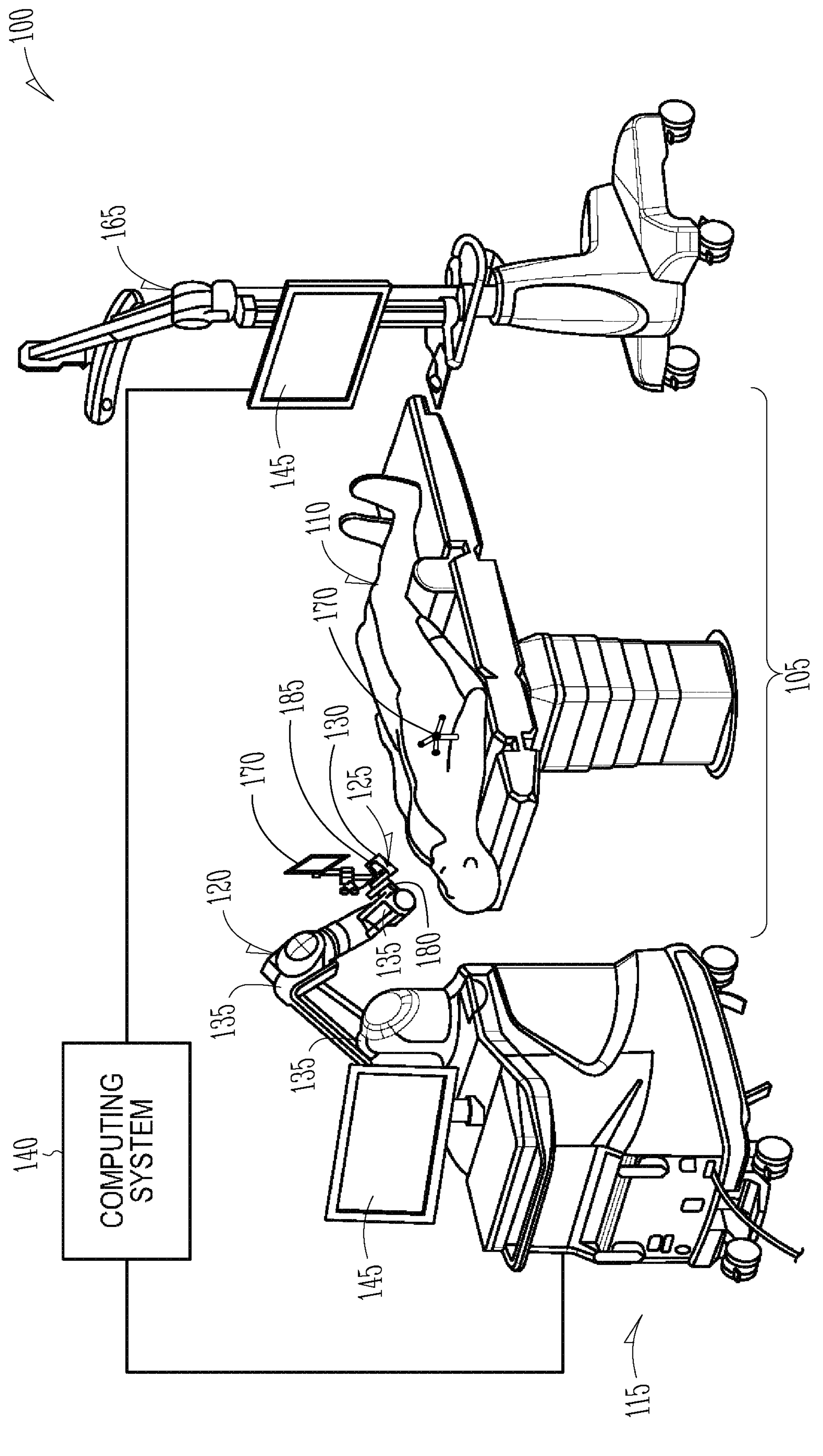
FIG. 1A is a diagrammatic view of an operating room including a robot-assisted surgical system comprising a robotic arm, a computing system and a tracking system with which the systems, devices and methods of the present disclosure can be implemented.

FIG. 1A illustrates surgical system 100 for operation on surgical area 105 of patient 110 in accordance with at least one example of the present disclosure. In examples, surgical area 105 can include a joint, including one or more bones. Surgical area 105 can include any surgical area of patient 110, including but not limited to the shoulder, head, elbow, hip, ankle, thumb, spine, and the like. Surgical system 100 can also include robotic system 115 with one or more robotic arms, such as robotic arm 120. As illustrated, robotic system 115 can utilize only a single robotic arm. Robotic arm 120 can be a 6 degree-of-freedom (DOF) robot arm, such as the ROSA® robot from Medtech, a Zimmer Biomet Holdings, Inc. company. In some examples, robotic arm 120 can be cooperatively controlled with surgeon input on the end effector or surgical instrument, such as surgical instrument 125. In other examples, robotic arm 120 can operate autonomously. While not illustrated in FIG. 1A, one or more positionable surgical support arms can be incorporated into surgical system 100 to assist in positioning and stabilizing instruments or anatomy during various procedures.

Each robotic arm 120 can rotate axially and radially and can receive a surgical instrument, or end effector, 125 at distal end 130. Surgical instrument 125 can be any surgical instrument adapted for use by the robotic system 115, including, for example, a guide tube, a holder device, a gripping device such as a pincer grip, a burring device, a reaming device, an impactor device such as a humeral head impactor, a pointer, a force-limiting device, a probe or the like. Surgical instrument 125 can be positionable by robotic arm 120, which can include multiple robotic joints, such as joints 135, that allow surgical instrument 125 to be positioned at any desired location adjacent or within a given surgical area 105. Robotic arm 120 can be used with an instrument positioning device, e.g., an instrument holder, to position an instrument in a known, desired or predetermined orientation relative to surgical area 105 based on a virtual coordinate system determined by computing system 140.

Robotic system 115 can also include computing system 140 that can operate robotic arm 120 and surgical instrument 125. Computing system 140 can include at least memory, a processing unit, user input devices, output devices, communications devices, and the like. Computing system 140 and tracking system 165 can also include human interface devices 145 for providing images for a surgeon to be used during surgery. Computing system 140 is illustrated as a separate standalone system, but in some examples computing system 140 can be integrated into robotic system 115. Human interface devices 145 can provide images, including but not limited to three-dimensional images of bones, a glenoid, joints, prostheses, and the like, as well as bone density information for generic bones and specific bones of a patient. Human interface devices 145 can include associated input mechanisms, such as a touch screen, foot pedals, or other input devices compatible with a surgical environment.

Computing system 140 can receive pre-operative, intra-operative and post-operative medical images. These images can be received in any manner and the images can include, but are not limited to, computed tomography (CT) scans, magnetic resonance imaging (MRI), two-dimensional x-rays, three-dimensional x-rays, ultrasound, and the like. As discussed herein, these images can include, or can be modified to include, bone density information that can be used to, for example, produce three-dimensional models of anatomy of a specific patient that can indicate three-dimensional bone density. The images and three-dimensional bone density models, in examples, can be sent via a server as files attached to an email. In another example the images can be stored on an external memory device such as a memory stick and coupled to a USB port of the robotic system to be uploaded into the processing unit. In yet other examples, the images can be accessed over a network by computing system 140 from a remote storage device or service.

After receiving one or more images, computing system 140 can generate one or more virtual models related to surgical area 105, such as a three-dimensional model incorporating, for example, bone density or anatomy information. Alternatively, computing system 140 can receive virtual models of the anatomy of the patient prepared remotely. Specifically, a virtual model of the anatomy of patient 110 can be created by defining anatomical points within the image(s) and/or by fitting a statistical anatomical model to the image data. In examples, the virtual model can comprise a finite element model. Additionally, the virtual model can be created using multiple orthogonal x-ray images of the anatomy of the patient merged together to form a three-dimensional model. The virtual model, along with virtual representations of implants, can be used for calculations related to the desired height, depth, inclination angle, or version angle of an implant, stem, surgical instrument, or the like related to be utilized in surgical area 105. In another procedure type, the virtual model can be utilized to determine insertion location, trajectory, insertion force (e.g., an insertion force ceiling to avoid adversely affecting bone structure of a specific patient) and depth for inserting an instrument. The virtual model can also be used to determine bone dimensions, implant dimensions, bone fragment dimensions, bone fragment arrangements, and the like. Any model generated, including three-dimensional models, can be displayed on human interface devices 145 for reference during a surgery or used by robotic system 115 to determine motions, actions, and operations of robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mahfouz, as well as other techniques known in the art.

The virtual models and three-dimensional models can include patient-specific information, such as age, gender, ethnicity, height, weight, activity level and the like. The patient-specific, three-dimensional bone models can be used to, for example, 1) determine various prostheses compatible with anatomy, e.g., soft tissue anatomy including bone density information, of the imaged patient, 2) determine locations for bone modifications in order to prepare the bone to receive a prosthetic device accounting for the density of the bone matter, 3) determine fit and fixation of a selected prosthesis with bone matter of the patient based on density of the bone matter, and 4) determine post-operative outcomes for the selected parameters of 1)-3) based on, for example, particular activities of the imaged patient.

Computing system 140 can also communicate with tracking system 165 that can be operated by computing system 140 as a stand-alone unit. Surgical system 100 can utilize the Polaris optical tracking system from Northern Digital, Inc. of Waterloo, Ontario, Canada. Additionally, tracking system 165 can comprise the tracking system shown and described in Pub. No. US 2017/0312035, titled "Surgical System Having Assisted Navigation" to Brian M. May, which is hereby incorporated by this reference in its entirety. Tracking system 165 can monitor a plurality of tracking elements, such as tracking elements 170, affixed to objects of interest to track locations of multiple objects within the surgical field. Tracking system 165 functions to create a virtual three-dimensional coordinate system within the surgical field for tracking patient anatomy, surgical instruments, or portions of robotic system 115. Tracking elements 170 can be tracking frames including multiple IR reflective tracking spheres, or similar optically tracked marker devices. In one example, tracking elements 170 can be placed on or adjacent one or more bones of patient 110. In other examples, tracking elements 170 can be placed on robotic arm 120, surgical instrument 125, and/or an implant to accurately track positions within the virtual coordinate system associated with surgical system 100. In each instance tracking elements 170 can provide position data, such as patient position, bone position, joint position, robotic arm position, implant position, or the like.

Robotic system 115 can include various additional sensors and guide devices. For example, robotic system 115 can include one or more force sensors, such as force sensor 180. Force sensor 180 can provide additional force data or information to computing system 140 of robotic system 115. Force sensor 180 can be used by a surgeon to cooperatively move robotic arm 120. For example, force sensor 180 can be used to monitor impact or implantation forces during certain operations, such as insertion of an implant stem into a intramedullary canal. Monitoring forces can assist in preventing negative outcomes through force fitting components. In other examples, force sensor 180 can provide information on soft-tissue tension in the tissues surrounding a target joint. In certain examples, robotic system 115 can also include laser pointer 185 that can generate a laser beam or array that is used for alignment of implants during surgical procedures.

In order to ensure that computing system 140 is moving robotic arm 120 in a known and fixed relationship to surgical area 105 and patient 110, the space of surgical area 105 and patient 110 can be registered to computing system 140 via a registration process involving registering fiducial markers attached to patient 110 with corresponding images of the markers in patient 110 recorded preoperatively or just prior to a surgical procedure. For example, a plurality of fiducial markers can be attached to patient 110, images of patient 110 with the fiducial markers can be taken or obtained and stored within a memory device of computing system 140. Subsequently, patient 110 with the fiducial markers can be moved into, if not already there because of the imaging, surgical area 105 and robotic arm 120 can touch each of the fiducial markers. Engagement of each of the fiducial markers can be cross-referenced with, or registered to, the location of the same fiducial marker in the images. In additional examples, patient 110 and medical images of the patient can be registered in real space using contactless methods, such as by using a laser rangefinder held by robotic arm 120 and a surface matching algorithm that can match the surface of the patient from scanning of the laser rangefinder and the surface of the patient in the medical images. As such, the real-world, three-dimensional geometry of the anatomy attached to the fiducial markers can be correlated to the anatomy in the images and movements of instruments 125 attached to robotic arm 120 based on the images will correspondingly occur in surgical area 105.

Subsequently, other instruments and devices attached to surgical system 100 can be positioned by robotic arm 120 into a known and desired orientation relative to the anatomy to implant a selected prosthesis according to the selected operative plan. The location where robotic arm 120 holds instruments and where associated resections or bone alterations are placed on a bone can be planned using patient-specific soft tissue information.

Surgical system 100 and in particular computing system 140 can be used to provide pre-operative and intra-operative feedback regarding fixation of implants into bone matter based on the various electronics and sensors described herein. The feedback can comprise an impaction force, acceleration data, and other sensor data that can be used, e.g., analyzed and evaluated, to determine implantation, impaction, proper seating and the like of prosthetic devices. The impaction force can be compared to threshold impaction force data stored in a controller or elsewhere that correlates impaction force to proper seating or assembly of prosthetic devices. The feedback can also provide post-operative feedback to provide data relating to patient activity and use of the implanted prosthetic device. Such, post-operative data can comprise pressure, force, strain, pH, temperature, acceleration, and the like. The feedback can be provided to an external interrogation device and can be in the form of visual indicators, such as heat maps, risk scales, color coding and the like to inform a surgical team about specific risks for a specific patient. Furthermore, the feedback can comprise discrete recommendations, such as no-go or go recommendations for specifically planned implant scenarios. In examples, the feedback can be compared to historical data sets collected from procedures performed on similar patients. In examples, the feedback can be connected to data sets from other technology applications along the patient continuum of care. For example, feedback and data from a plurality of sensors, including sensors of the present disclosure, can be compared to software-based pre-operative planning and intra-operative data, such as from robotic surgical systems, e.g., positioning data, to inform the surgeon about which implant designs, sizes, and surgical approaches yield favorable clinical results for individual patients and future patients.

Figure 1B:
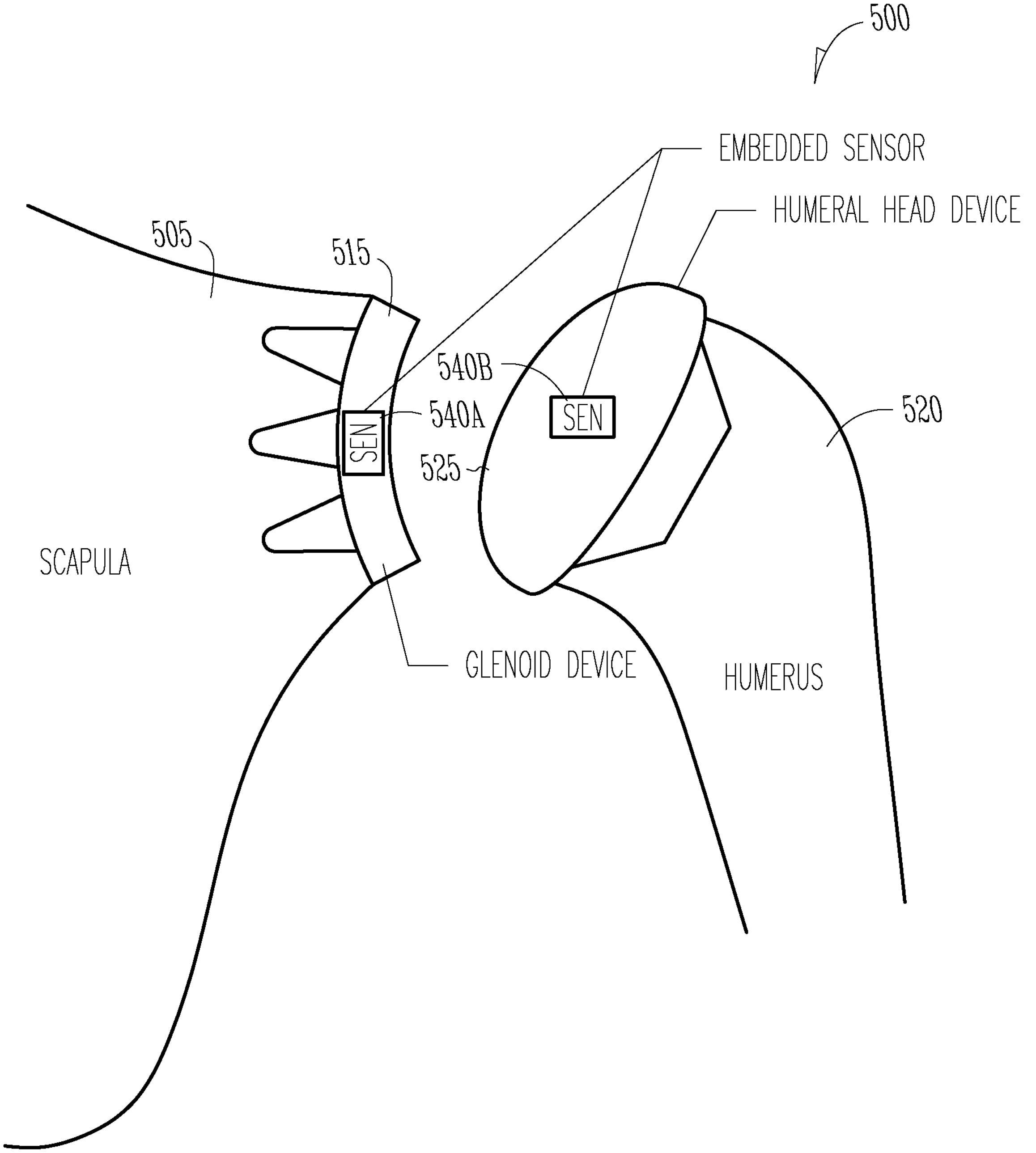
FIG. 1B is a diagram illustrating an anatomic shoulder arthroplasty with sensors embedded in prostheses, according to some example embodiments.

FIG. 1B is a diagram illustrating a total shoulder arthroplasty with sensors embedded in prostheses, according to some example embodiments. The total shoulder arthroplasty system 500 includes a glenoid component 515 affixed to the scapula 505 with a glenoid component including an embedded sensor 540A. On the humeral side, the total shoulder arthroplasty system 500 includes humeral prosthesis 525 affixed within the humerus 520 including an embedded sensor 540B. The embedded sensors can optionally be encased within the components or removable modules. In some examples, the sensors are integral within the components. In an example, the sensors, such as embedded sensors 540A, 540B, communicate data wirelessly to a computing device, which can then analyze the data to provide feedback to the surgeon. In another example, a first of embedded sensors 540A and 540B can communicate data to a second of embedded sensors 540A and 540B while the second embedded sensor then communicates the data wirelessly to a computing device. For example, relative position data between embedded sensors 540A and 540B (and vice versa) can be transmitted to the computing device to indicate how that location data changes over time. In examples, sensors 540A, 540B can comprise force sensors and can be configured to receive force transmitted between the glenoid component 515 and the humeral prosthesis 525, such as when the shoulder is reduced to check joint tension with the prostheses in place or post-operatively during patient recovery and beyond. Such data can be tied to clinical outcomes such as acromial stress fractures or dislocation to, for example, determine optimal joint tension. In some examples, a single embedded force sensor, such as embedded sensor 540A, is used to provide accurate force data for the joint. In other examples, multiple force sensors are embedded within different portions of the prostheses to provide additional information on loading patterns within the joint. For example, force sensors can be embedded around the periphery of a glenoid or humeral head component, which allows mapping of the force on different portions of the implantable component, as well a trial, throughout the entire range of motion. Pairs of embedded force sensors could also be used to measure range of motion and to measure wear of components, such as polymer bearings. As discussed herein, sensors 540A and 540B can be comprised of a plurality of sub-components that can be mounted to different portions of glenoid component 515 and a humeral prosthesis 525, respectively. Examples of humeral prosthesis 525 are discussed with reference to FIGS. 2A-9. In examples, total shoulder arthroplasty system 500 can comprise the devices as described in U.S. Pat. No. 10,966,788, titled "Sensor-based shoulder system and method" to Orsa Britton et al., the contents of which are hereby incorporated by reference.

Figure 2A:
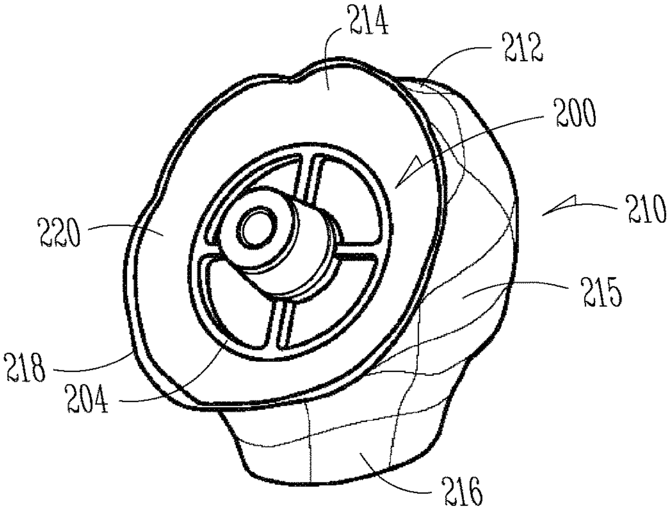
FIG. 2A is a perspective view of a resected humeral head of a humerus bone having an anchor of a stemless humeral head prosthetic implanted therein.
Figure 2B:
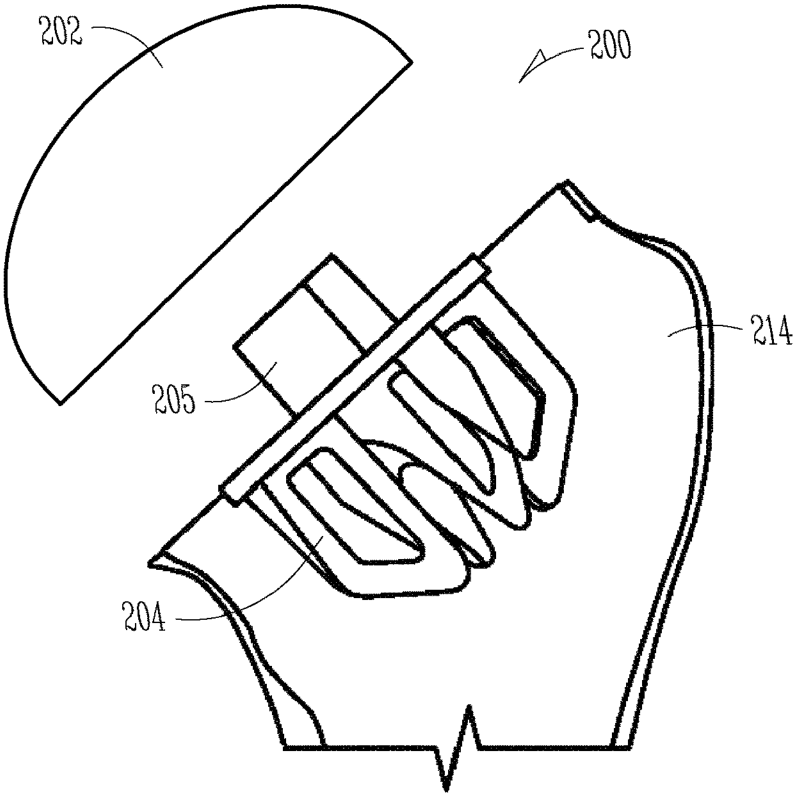
FIG. 2B is a side view of the humeral head of FIG. 2A showing the anchor of the stemless humeral head prosthetic having fixation fins inserted into cancellous bone.

FIG. 2A is a perspective view of a resected humeral head of a humerus bone having a humeral arthroplasty prosthesis 200 implanted therein. FIG. 2B is a side view of humeral arthroplasty prosthesis 200 of FIG. 2A showing humeral head prosthesis 202 and stemless humeral anchor prosthesis 204. FIGS. 2A and 2B are discussed concurrently.

Stemless humeral anchor prosthesis 204 of humeral arthroplasty prosthesis 200 can be implanted into humerus 210. Humerus 210 can comprise humeral head 212 (FIG. 2A), tubercle area 215 and diaphysis region 216 (FIG. 2A). Humerus 210 can have a hard exterior formed of cortical bone 218 and a softer interior formed of cancellous bone 220. Humeral head 212 can be resected to from cut surface 214 that can expose cancellous bone 220. Though the present application is discussed with reference to bones of a shoulder joint, the systems, devices and methods of the present disclosure can be used to in conjunction with other bones and joints, such as ankle, knee and hip joints.

Stemless humeral anchor prosthesis 204 of humeral arthroplasty prosthesis 200 can be attached to humerus 210 via insertion of stemless humeral anchor prosthesis 204 into cancellous bone 220. Stemless humeral anchor prosthesis 204 can include taper or taper adapter 205 that can be coupled to humeral head prosthesis 202. Stemless humeral anchor prosthesis 204 can be positioned so that humeral head prosthesis 202 contacts or is in close proximity to cut surface 214.

Humeral head prosthesis 202 and stemless humeral anchor prosthesis 204 can be fabricated of typical materials for prosthetic implants, such as titanium, cobalt chrome, or stainless steel. Such materials can be hard and as such are desirable to reduce wear and prevent damage or corrosion. However, such hard materials can be significantly harder than the bone material to which they are attached. Stemless humeral anchor prosthesis 204 can prevent damage to humerus 210, particularly during the implant procedures, by avoiding placement of long stems into cancellous bone 220 that can potentially crack or damage the cortical bone when impacted with a hammer or mallet. As such, humeral arthroplasty prosthesis 200 can be compact in shape and can include a plurality of fins, blades, projections, fingers or wings that can engage cancellous bone 220 without having to significantly modify humerus 210. Such fins, blades, projections, fingers or wings can be used as platforms for mounting electronic components that are advantageously placed in contact with bone or away from metal components, while other electronics components can be positioned within humeral head prosthesis 202, as is discussed with reference to FIGS. 3A-5.

In additional examples, humeral arthroplasty prosthesis 200 can be used in conjunction with a glenoid prosthesis device that can be implanted into a scapula or the patient receiving humeral arthroplasty prosthesis 200, as shown in FIG. 1B. Such glenoid prostheses can include sensors for collecting data from the glenoid prosthetic and the surrounding anatomy. Glenoid prosthesis devices can include sensors to collect various data relating to temperature, acceleration, position and the like. As is discussed herein, sensor data from humeral arthroplasty prosthesis 200 and the glenoid prosthesis can be used in conjunction with each other to provide feedback to the patient or medical professional. In examples, the relative position between humeral arthroplasty prosthesis 200 and the glenoid prosthesis can be determined from sensor data, such as positions sensors, proximity sensors, accelerometers, gyroscopes and the like. The relative position data can be used to determine assembly of the prosthetic devices, movement of the prosthetic device over time, wear of the prosthetic devices, range of motion of the joint and the like.

Figure 3A:
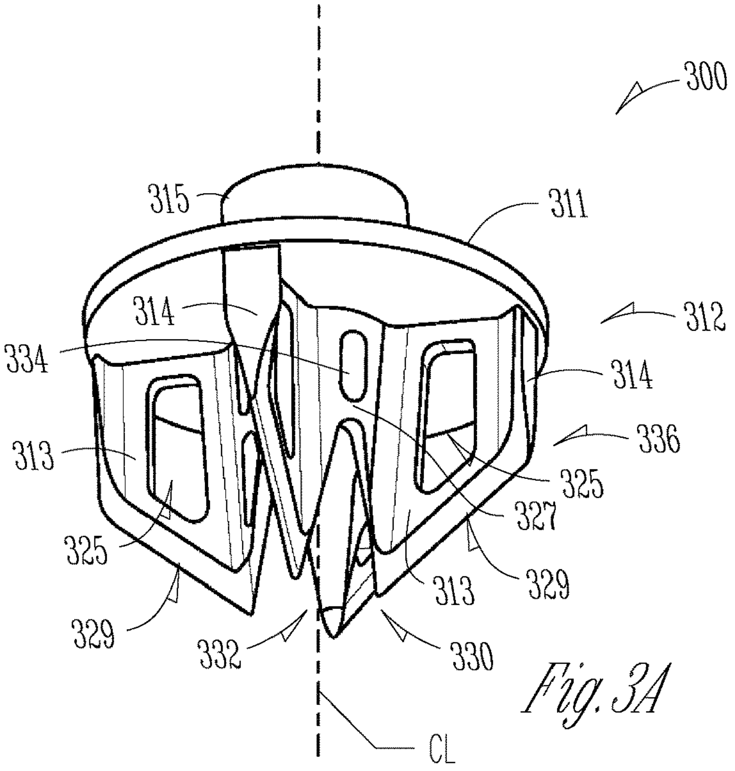
FIG. 3A is a perspective bottom view of a stemless humeral head implant showing fixation fins.
Figure 3B:
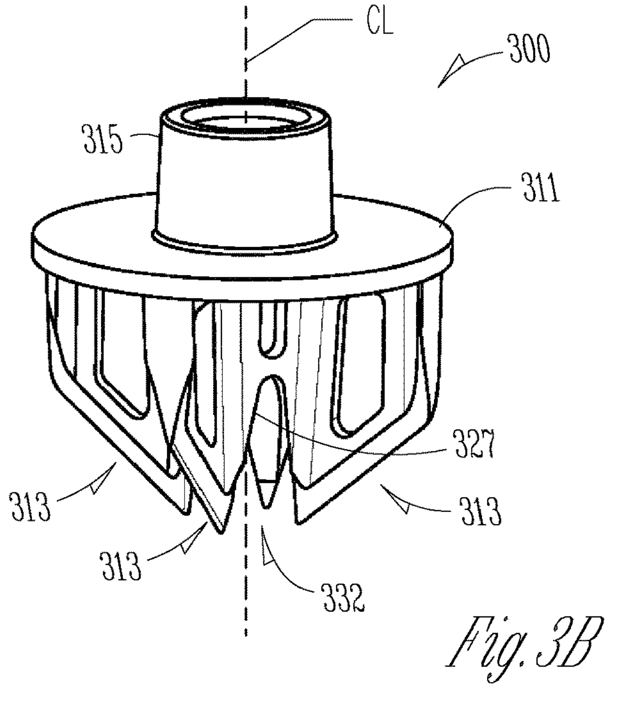
FIG. 3B is a perspective top view of the stemless humeral head implant of FIG. 3A showing a coupler for a humeral head prosthesis.

FIG. 3A is a perspective view of humeral anchor prosthesis 300. FIG. 3B is a perspective top view of humeral anchor prosthesis 300 of FIG. 3A showing connection portion 315 for a humeral head prosthesis. FIGS. 3A and 3B are discussed concurrently. Humeral anchor prosthesis 300 can comprise a stemless humeral anchor prosthesis. Humeral anchor prosthesis 300 can comprise base plate 311 and blades 313. In examples, humeral anchor prosthesis 300 can comprise the humeral head implant described in U.S. Pat. No. 8,992,623, titled “Shoulder Prosthesis” to Andrew Hopkins et al., the contents of which are hereby incorporated by reference.

Humeral anchor prosthesis 300 can comprise base plate 311, which can comprise a circular disk having a first proximal side and a second distal side connected by an edge surface or rim. Connection portion 315 can extend from the first side of base plate 311 in a first direction and blades 313 can extend from a second side of base plate 311 in a second direction. Connection portion 315 can comprise a stud or receptacle for attaching a prosthetic humeral head (e.g., humeral head prosthesis 202 of FIG. 2B) to base plate 311. In examples, connection portion 315 can comprise a tapered cylinder-like body. However, connection portion 315 can comprise any suitable connection means to reliably connect the humeral head to humeral anchor prosthesis 300.

The distal side of base plate 311 can be provided with anchoring means 312 that serve to reliably anchor humeral anchor prosthesis 300 in the humerus bone of a patient. Anchoring means 312 can comprise blades 313 extending from base plate 311. In examples, four blades 313 can be used. However, in other examples, a greater number of blades 313 or a lesser number of blades 313 can be used. In examples, blades 313 can comprise ribs or shanks having planar sidewalls that extend perpendicularly from base plate 311. In examples, blades 313 can be evenly distributed in a circumferential direction around central axis C. In examples having four blades 313, the angle between neighboring blades 313 can be 90°. However, other angles can be provided between neighboring blades 313 and the angles between all blades 313 need not be equal. Blades 313 can extend in a radial direction from central axis C. In examples of the present disclosure, the configuration of prosthetic implants can be customized for specific patients. For example, the number and orientation of blades 313 can be selected based on bone density information of a specific patient.

Blades 313 can be provided with openings 325. Openings 325 can improve blood circulation and osseointegration of humeral anchor prosthesis 300. Moreover, openings 325 and space 332 can help minimize the size of humeral anchor prosthesis 300 thereby minimizing the surgical impact of humeral anchor prosthesis 300 while at same time promoting osseointegration. In examples, one or more of openings 325 can be used to house or provide support to electronics components of the present disclosure. For example, a sensor, such as a temperature sensor, pH, can be positioned in an opening 325 to reduce the amount of electronics stored in a prosthetic head component, e.g., humeral head prosthesis 202, and to advantageously position such sensor in contact with bone matter.

The radially inner ends 330 of neighboring blades 313 can be connected by webs 327. Webs 327 can extend distally from base plate 311 and can have lengths shorter than blades 313. Webs 327 can enclose central space 332 adjacent to base plate 311 that is free of protrusions. Therefore, in an implanted state of humeral anchor prosthesis 300, material of the humerus bone can extend into space 332 promoting osseointegration. To foster this process, webs 327 can be provided with openings 334 which can, among other things, improve blood circulation in regions adjacent to humeral anchor prosthesis 300. In particular, openings 334 can allow circulation of blood into and out of the bony material disposed in free central space 332. In examples, central space 332 can be provided with electronics components as described herein, such as antenna elements or sensor elements.

The radially outer ends 336 of blades 313 can be provided with wings 314 that extend in in a circumferential direction. In examples, wings 314 can be disposed flush with the outer contour of base plate 311. Wings 314 can improve anchoring properties of blades 313 and contribute, as with webs 327, to the stability and stiffness of humeral anchor prosthesis 300.

The distal edges of wings 314 and blades 313 can form cutting edges 329 that can facilitate implantation of humeral anchor prosthesis 300. Distal edges of webs 327 are illustrated as not having cutting edges, but can be provided with cutting edges in other examples.

The geometry of blades 313 can be such that humeral anchor prosthesis 300 resembles, in a side view, the shape of an arrowhead, i.e. the distal edges of blades 313 can recede in a radial direction towards the radially outer end 336 of blades 313. The edges of radially inner ends 330 of blades 313 can be inclined with respect to central axis C. In other words, the radially inner edges of blades 313 diverge when viewed along central axis C from a distal surface of base plate 311, i.e., when viewed from proximal to distal. Free central space 332 can, therefore, have a conical shape tapering towards base plate 311.

Figure 4:
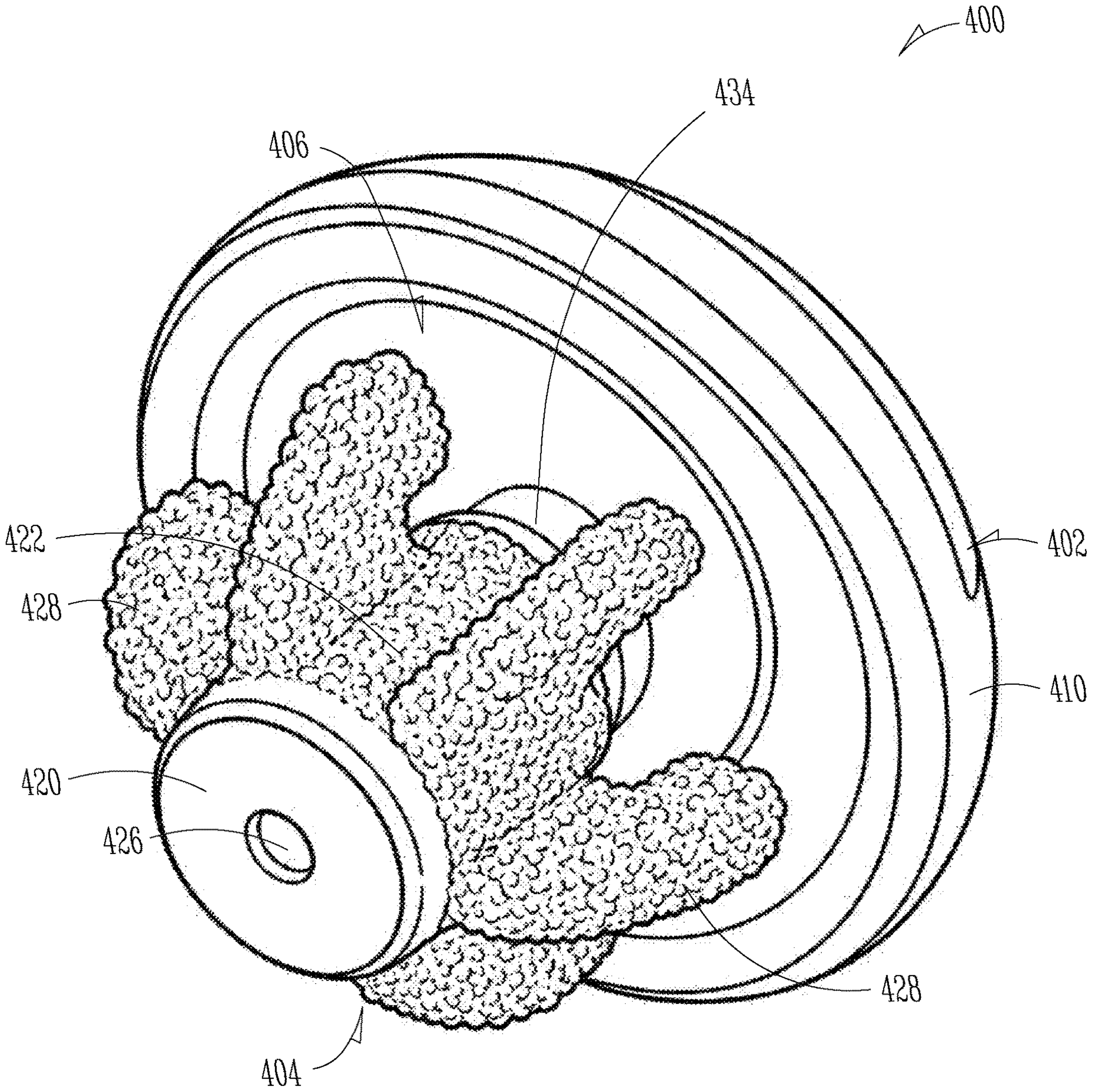
FIG. 4 is a perspective bottom view of another example of a stemless humeral head prosthesis having projections.
Figure 5:
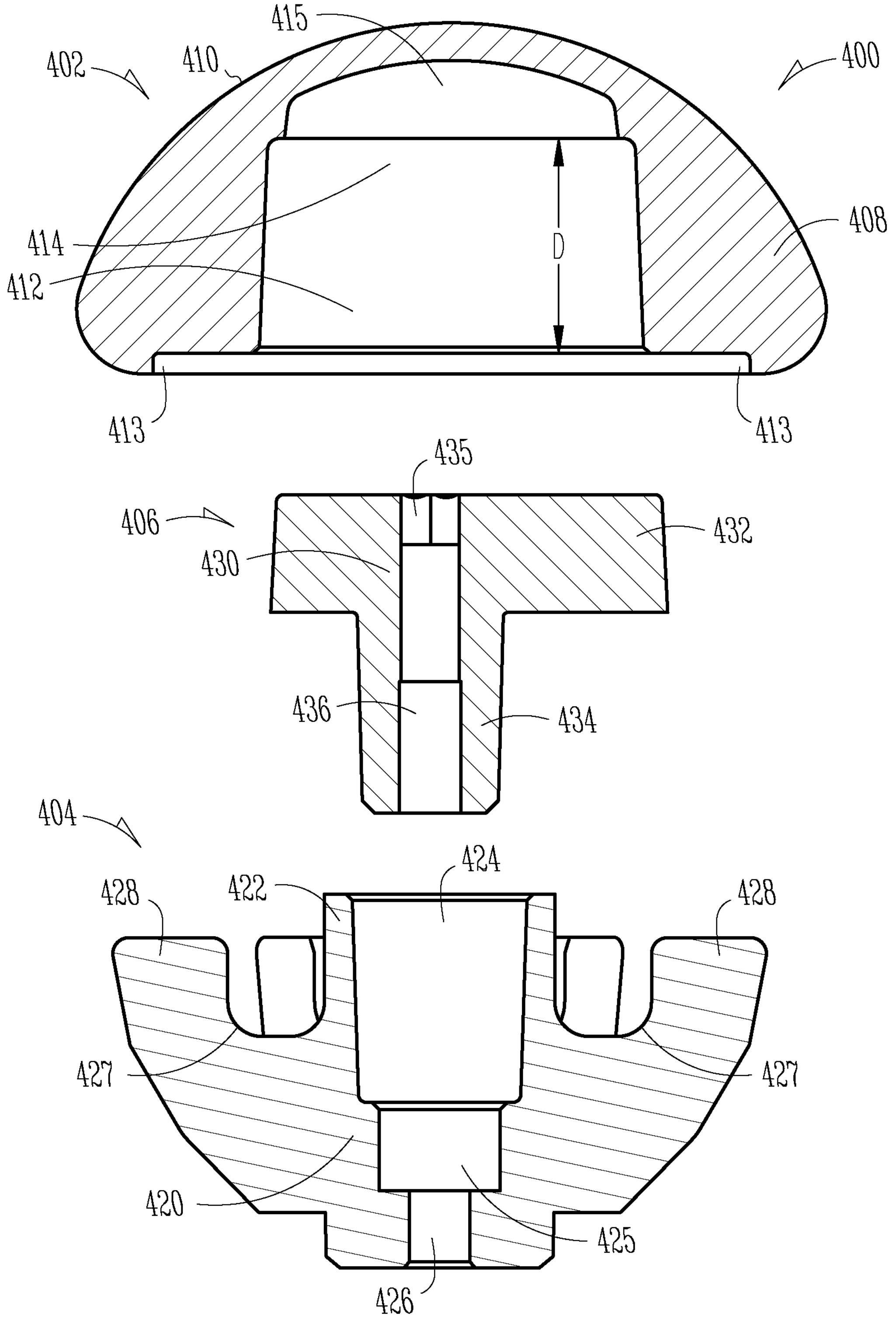
FIG. 5 is an exploded view of the stemless humeral head prosthesis of FIG. 4 showing a humeral head component, an adapter component and a stemless anchor component.

FIG. 4 is a perspective bottom view of stemless humeral prosthesis 400 comprising prosthetic head component 402, stemless anchor component 404 and adapter component 406. FIG. 5 is an exploded view of stemless humeral prosthesis 400 of FIG. 4 showing prosthetic head component 402, stemless anchor component 404 and adapter component 406. In examples, stemless humeral prosthesis 400 can comprise the humeral head implant described in U.S. Pat. No. 8,506,638, titled "Shoulder Prosthesis" to Thomas M. Vanasse et al., the contents of which are hereby incorporated by reference. FIGS. 4 and 5 are discussed concurrently.

Prosthetic head component 402 can comprise head body 408, bearing surface 410, adapter socket 412, proximal surface 413, upper chamber 414 and pocket 415.

Stemless anchor component 404 can comprise anchor body 420, extension 422, adapter socket 424, intermediate passage 425, distal socket 426, pockets 427 and projections 428.

Adapter component 406 can comprise adapter body 430, plate 432, projection 434, driver socket 435 and passage 436.

Head body 408 can comprise a hemispherical or partial-spherical body having bearing surface 410 configured to articulate, e.g., slide, against a mating prosthetic or natural glenoid. Head body 408 can be fabricated of a hard material, such as stainless steel, Titanium, CoCr or another metal. Adapter socket 412 can extend into proximal surface 413. Adapter socket 412 can be configured to receive plate 432 of adapter component 406 in order to couple prosthetic head component 402 to adapter component 406. Plate 432 can fit within adapter socket 412 with an interference fit, such as a press fit or force fit. Adapter socket 412 can be tapered to receive a correspondingly tapered plate 432. Adapter socket 412 can have depth D. Socket 412 can be configured to receive the full thickness of plate 432. The length of depth D can additionally be increased to remove weight from head body 408, such as by providing pocket 415. Pocket 415 can be smaller in diameter than socket 412 and can have a curved outer wall in order to fit within the geometry of bearing surface 410. As is discussed in greater detail below, socket 412, upper chamber 414 and pocket 415 can be utilized as storage space for various electronics modules, components and elements, including sensors and power sources.

Projection 434 can extend from plate 432 and can be configured to be inserted into adapter socket 424 of stemless anchor component 404 so that stemless anchor component 404 can be coupled to adapter component 406. Projection 434 can fit within adapter socket 424 with an interference fit, such as a press fit or force fit. As is known in the art, projection 434 can be located off-center from plate 432 so that the position of prosthetic head component 402 relative to stemless anchor component 404 can be varied to accommodate different anatomic geometries. Passage 436 can extend through adapter component 406 from plate 432 through projection 434. Passage 436 can include driver socket 435, e.g., a hex socket, at plate 432 to facilitate rotation of adapter component 406 relative to stemless anchor component 404. In examples, one or both of projection 434 and adapter socket 424 can be threaded to facilitate assembly and disassembly.

Extension 422 of stemless anchor component 404 can comprise a cylindrical body for receiving projection 434. Extension 422 can extend from anchor body 420. Adapter socket 424 can be tapered to receive a correspondingly tapered projection 434. Stemless anchor component 404 can additionally include distal socket 426 that can connect to adapter socket 424 via intermediate passage 425. Distal socket 426 and intermediate passage 425 can allow for access to driver socket 435 and adapter socket 412 from the distal end of stemless anchor component 404 and stemless humeral prosthesis 400. Distal socket 426 and intermediate passage 425 can facilitate disassembly of stemless humeral prosthesis 400. Projections 428 can extend from anchor body 420 in a radial manner to provide anchoring within bone matter. In the illustrated example, stemless anchor component 404 can comprise six equally spaced projections 428. Projections 428 can additionally be axially curved to form pockets 427 over which bone matter can grow to retain stemless anchor component 404 within bone. Anchor body 420 and extension 422 can be fabricated of any suitable material, such as stainless steel. In examples, anchor body 420 can be fabricated from or coated with a porous material to facilitate bone in-growth. As discussed in greater detail below, stemless anchor component 404, as well as other components described herein, can provide a platform or frame upon which to mount various electronics modules, components and elements. For example, electronics components, such as antennas, can be mounted to distal socket 426 so as to be located away from humeral head prosthesis 202, which can be fabricated from materials that can shield or inhibit transmission of communication signals. Additionally, projections 428 can be used to mount electronics components that benefit from direct contact with bone matter, such as sensors. Furthermore, as discussed in greater detail below, any or all of prosthetic head component 402, stemless anchor component 404 and adapter component 406 can be fabricated of material that can facilitate the transmission of electrical signals. As such, prosthetic head component 402, stemless anchor component 404 and adapter component 406 can act as a communications conduit between electronics modules. Examples of materials suitable for transmission of electrical signals include, but are not limited to, stainless steel alloys, cobalt-based alloys and titanium-based alloys.

The present disclosure can provide stemless prosthetic devices, such as stemless humeral head prostheses, stemless femoral head prostheses and the like, that can incorporate electronics modules having sensors and communication devices without having to alter the outer envelope of the prosthetic devices, e.g., the shape of the prosthetic component that will interact with surrounding anatomy. In examples, the stemless, sensor-enabled prosthetic devices can incorporate two or more discrete electronics components that can be connected to two or more discrete implant components via lead wires or extensions that allow the discrete electronics components to be separated by space but connected electrically. Additionally, the two or more discrete components can be in electronic communication with each other via conductive properties of the material of the components, thereby reducing or eliminating the need for separate wiring. As can be seen in FIG. 5, for example, adapter socket 412 and upper chamber 414 can be configured to provide space for incorporating electronics components. Likewise, stemless anchor component 404 can be configured to provide a platform for mounting of electronics components that are on the exterior of stemless humeral head prosthesis and exposed to bone. Passage 436 can be configured as a conduit to facilitate coupling, e.g., electronic communication, between the electronics components mounted to stemless anchor component 404 and prosthetic head component 402.

Figure 6:
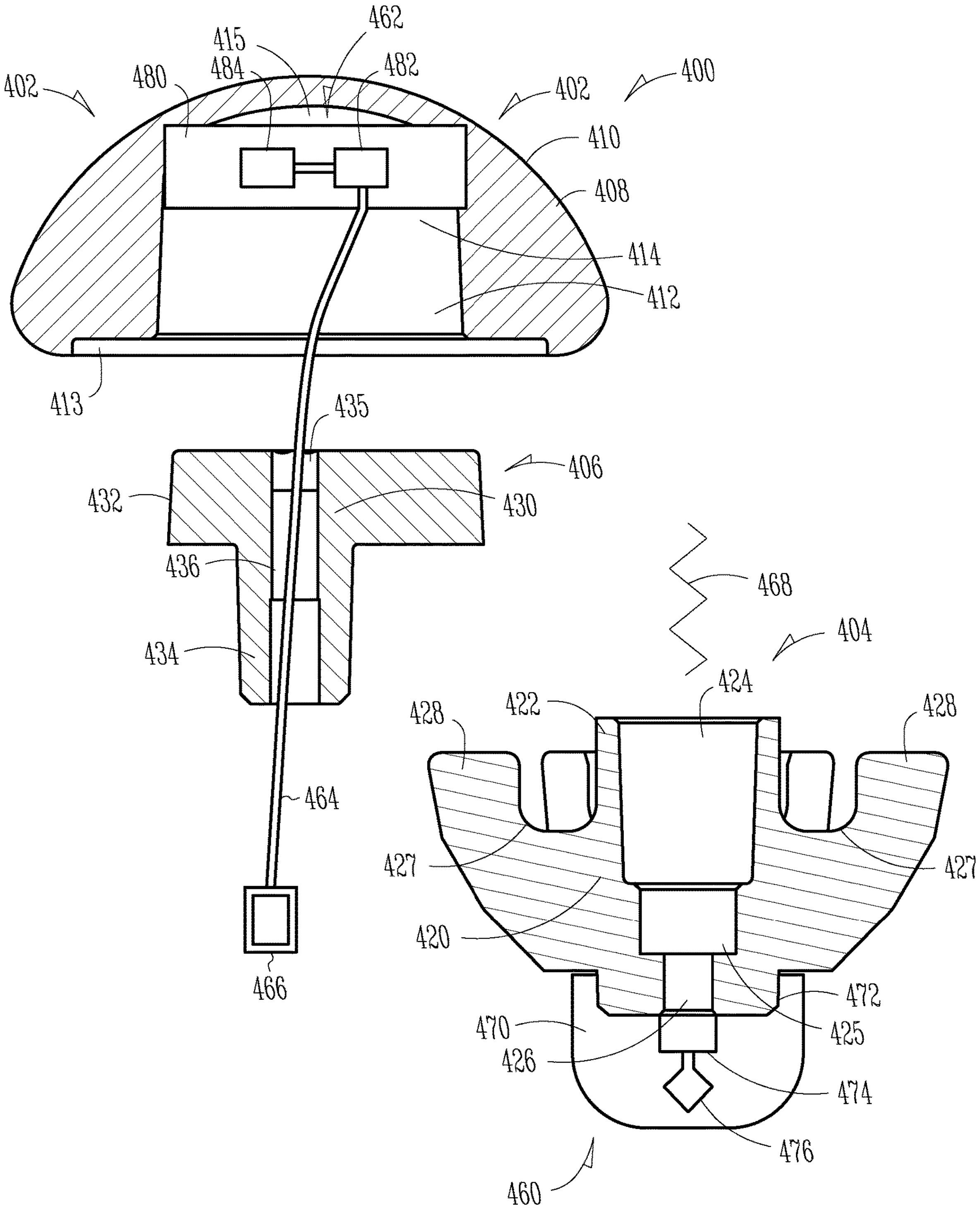
FIG. 6 is a side cross-sectional view of an exploded stemless humeral head implant having an antenna attached to an anchor component, an electronics module connected to a humeral head component and an adapter component having an electrical lead extending therethrough.

FIG. 6 is a side cross-sectional view of stemless humeral prosthesis 400 in an exploded state and having antenna module 460 attached to anchor component 404, electronics module 462 connected to prosthetic head component 402 and adapter component 406 having electrical lead 464 extending therethrough. Electrical lead 464 can extend between electronics module 462 at a first end and connector 466 at a second end.

Antenna module 460 can comprise housing 470, coupling socket 472, electrical socket 474 and antenna element 476. Antenna module 460 can comprise a capsule in which other components are mounted. In examples, antenna module 460 can be attached to stemless anchor component 404 at socket 424, intermediate passage 425 or distal socket 426. In the illustrated example, housing 470 can include coupling socket 472, which can comprise a female receptacle having internal threading configured to receive external threading on stemless anchor component 404. Electrical socket 474 can be configured to align with distal socket 426. Electrical socket 474 can provide electrical contact with antenna element 476. Antenna element 476 can comprise a coil or winding configured to interact with a wireless or radio signal. In examples, antenna element 476 can comprise a communication device, such as a Bluetooth® or Wi-Fi antenna. In examples, antenna element 476 can comprise any component or element that requires or otherwise benefits from interaction with an external wireless or radio signal. In the illustrated example, antenna element 476 is inside of housing 470. However, in other examples, antenna element 476 can be exposed to the exterior of housing 470. Housing 470 can be fabricated from a biocompatible material that can also allow or facilitate transmission of communications signals from and to antenna element 476. In examples, housing 470 can be fabricated of a polymer or plastic, such as PEEK. Housing 470 can have a curved distal end that forms a nosecone to facilitate pushing of antenna module 460 into bone matter.

Connector 466 can comprise an electrical connector configured to mate with electrical socket 474. In examples, connector 466 can comprise a male projection and electrical socket 474 can comprise a female receptacle. In examples, connector 466 and electrical socket 474 can comprise round components that can allow connection of housing 470 to stemless anchor component 404 for various radial orientations of housing 470. Connector 466 can be sized to fit within and pass through passage 436 and distal socket 426.

Electrical lead 464 can comprise a wire or bundle of wires connecting connector 466 to electronics module 462. Electrical lead 464 can comprise an insulation jacket or can comprise bare wires. Electrical lead 464 can include a security or strengthening cable to prevent connector 466 from being pulled apart from electronics module 462. Electrical lead 464 can be flexible to allow the distance between prosthetic head component 402 and stemless anchor component 404 to be varied, such as to allow assembly of stemless humeral prosthesis 400. For example, upon assembly of stemless humeral prosthesis 400, electrical lead 464 can be bunched between prosthetic head component 402 and stemless anchor component 404, such as within passage 436. As discussed in greater detail below, in examples, electrical lead 464 can be eliminated and electronic communication between electronics module 462 and antenna module 460, or another electronics component, can be conducted through the material of prosthetic head component 402, stemless anchor component 404 and adapter component 406. In yet additional examples, the electronic components within electronics module 462 can be separated into multiple sub-components that are in electronic communication with each other through the material of prosthetic head component 402, stemless anchor component 404 and adapter component 406. In these various examples, housing 480 and various sub-component housings can have openings or conductor ports that can engage the material of prosthetic head component 402, stemless anchor component 404 and adapter component 406 to allow the internal electronics components to contact the material of prosthetic head component 402, stemless anchor component 404 and adapter component 406.

Electronics module 462 can comprise housing 480, first electronics element 482 and second electronics element 484. Housing 480 can reside in socket 412 of prosthetic head component 402. Prosthetic head component 402 can be modified from the illustrated example of FIG. 5 to receive housing 480. For example, upper chamber 414 of prosthetic head component 402 can be widened and/or deepened or extended into pocket 415 to receive housing 480. Thus, in examples, the thickness of head body 408 can be reduced to receive housing 480 so as to not impact the outer dimensions of prosthetic head component 402. In the illustrated example, housing 480 is shown as a rectangle, but can have any shape. In examples, housing 480 can be configured to match the taper of socket 412 and upper chamber 414 and the curvature of pocket 415.

Housing 480 can comprise a structural element to contain and protect first electronics element 482 and second electronics element 484. In examples, housing 480 can be fabricated from a polymer or plastic. First electronics element 482 and second electronics element 484 can comprise any suitable elements desirable for producing sensing capabilities for stemless humeral prosthesis 400. In examples, first electronics element 482 and second electronics element 484 can comprise controllers, memory devices, communications devices, batteries, sensors, such as pressure sensors, temperature sensors, accelerometers, gyroscopes, thermometers, strain gages and the like, as well as other electronics components. Electronics module 462 is illustrated as having two electronics elements, but fewer or more elements can be used. As is discussed with reference to FIG. 9, electronics module 462 can include a plurality of different elements to obtain data from stemless humeral prosthesis 400 and surrounding anatomy. Furthermore, stemless humeral prosthesis 400 is shown having two electronics modules, antenna module 460 and electronics module 462 connected by a single electrical lead 464. However, in other examples, stemless humeral prosthesis 400 can have three or more electronics modules connected by two or more electrical leads. Thus, for example, electronics element 484 can be located remote from housing 480 via an electrical lead extending out of housing 480 from electronics element 482. In such example, electronics element 484 can comprise a sensor that benefits from directly contacting bone matter and can be mounted to one of projections 428.

In examples, electronics elements 482 can comprise a chain of sensors configured to sense the assembly of prosthetic head component 402 with adapter component 406 and assembly of adapter component 406 with stemless anchor component 404. In examples, such sensors can comprise resistance sensors placed on prosthetic head component 402, adapter component 406 and stemless anchor component 404 in series to sense electrical current flow through stemless humeral prosthesis 400 and contact of such components. The resistance measured by the resistance sensors can be measured over time to monitor assembly of stemless humeral prosthesis 400 such as to see if any of prosthetic head component 402, adapter component 406 and stemless anchor component 404 have maintained connection integrity. Similarly, resistance measurements can be used to measure impaction, and therefore assembly, of prosthetic head component 402 with adapter component 406 and assembly of adapter component 406 with stemless anchor component 404. For example, the amount of impaction can be characterized by the amount of electrical resistance through the components, whereby less resistance equates to more substantial impaction. In examples, the resistance can be measured directly through prosthetic head component 402, adapter component 406 and stemless anchor component 404. As such, a low resistance reading can be used to generate a signal that can be provided to the user, e.g. an audio, tactile or visual signal provided to the surgeon, to indicate that the components have been assembled with sufficient force. Furthermore, wear of any of prosthetic head component 402, adapter component 406 and stemless anchor component 404 can be extrapolated from the relative positions of prosthetic head component 402, adapter component 406 and stemless anchor component 404. In additional examples, springs, or other expandable conductors, can be positioned between prosthetic head component 402 and adapter component 406 and adapter component 406 and stemless anchor component 404 to form a continuous electrical path through stemless humeral prosthesis 400 even if separation occurs between any of prosthetic head component 402, adapter component 406 and stemless anchor component 404. For example, spring 468 can be positioned between, and attached to, adapter component 406 and stemless anchor component 404. As such, the electrical resistance through the springs can be compared to the electrical resistance through prosthetic head component 402, adapter component 406 and stemless anchor component 404 to look for differences. Additionally, real-time measurements can be taken during implantation of stemless humeral prosthesis 400 to ensure that impaction of prosthetic head component 402, adapter component 406 and stemless anchor component 404 has been performed at a sufficient level to provide proper assembly, e.g., seating, of prosthetic head component 402, adapter component 406 and stemless anchor component 404 such as by comparing to predetermined threshold impaction forces that are known to adequately assemble such components. Furthermore, position and other sensor data from a glenoid prosthesis can be used in conjunction with data from stemless humeral prosthesis 400 to evaluate assembly, relative positioning, wear and range of motion.

Figure 7A:
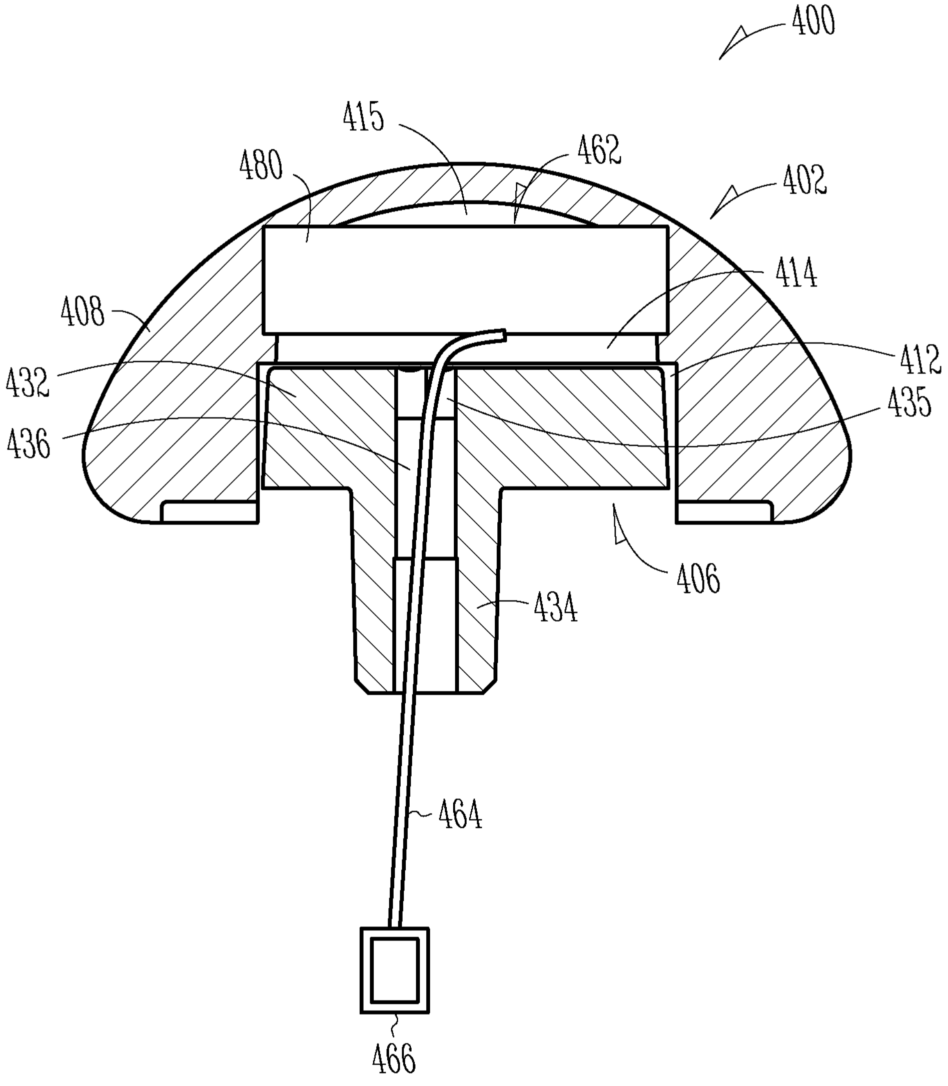
FIG. 7A is a first step of a process for assembling and implanting a sensor-enabled stemless humeral head implant of the present disclosure showing an adapter component positioned within a socket of a humeral head component and an electrical lead extending therefrom.
Figure 7B:
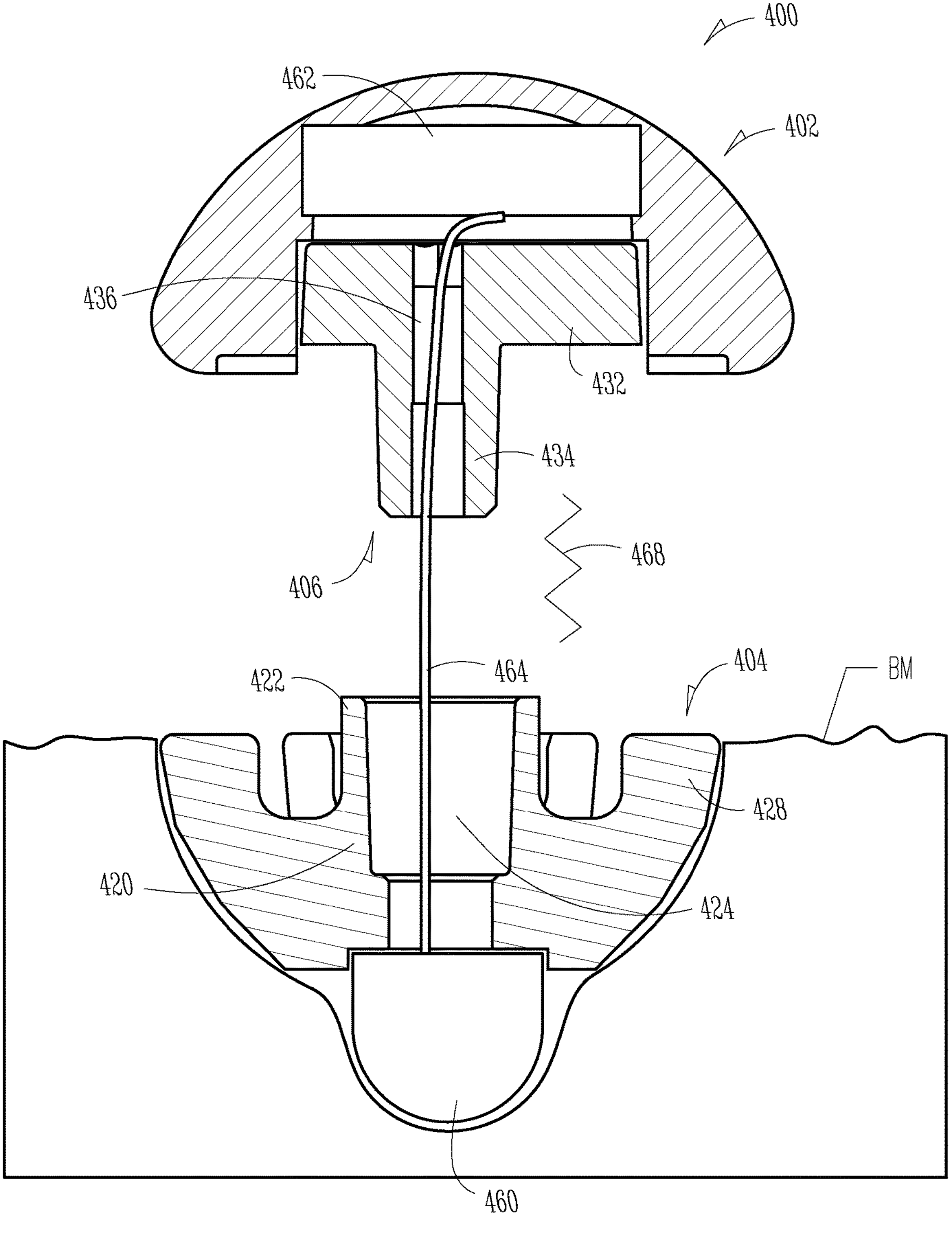
FIG. 7B is a second step of a process for assembling and implanting a sensor-enabled stemless humeral head implant of the present disclosure showing an electrical lead extended through the adapter component and coupled to a stemless anchor component.
Figure 7C:
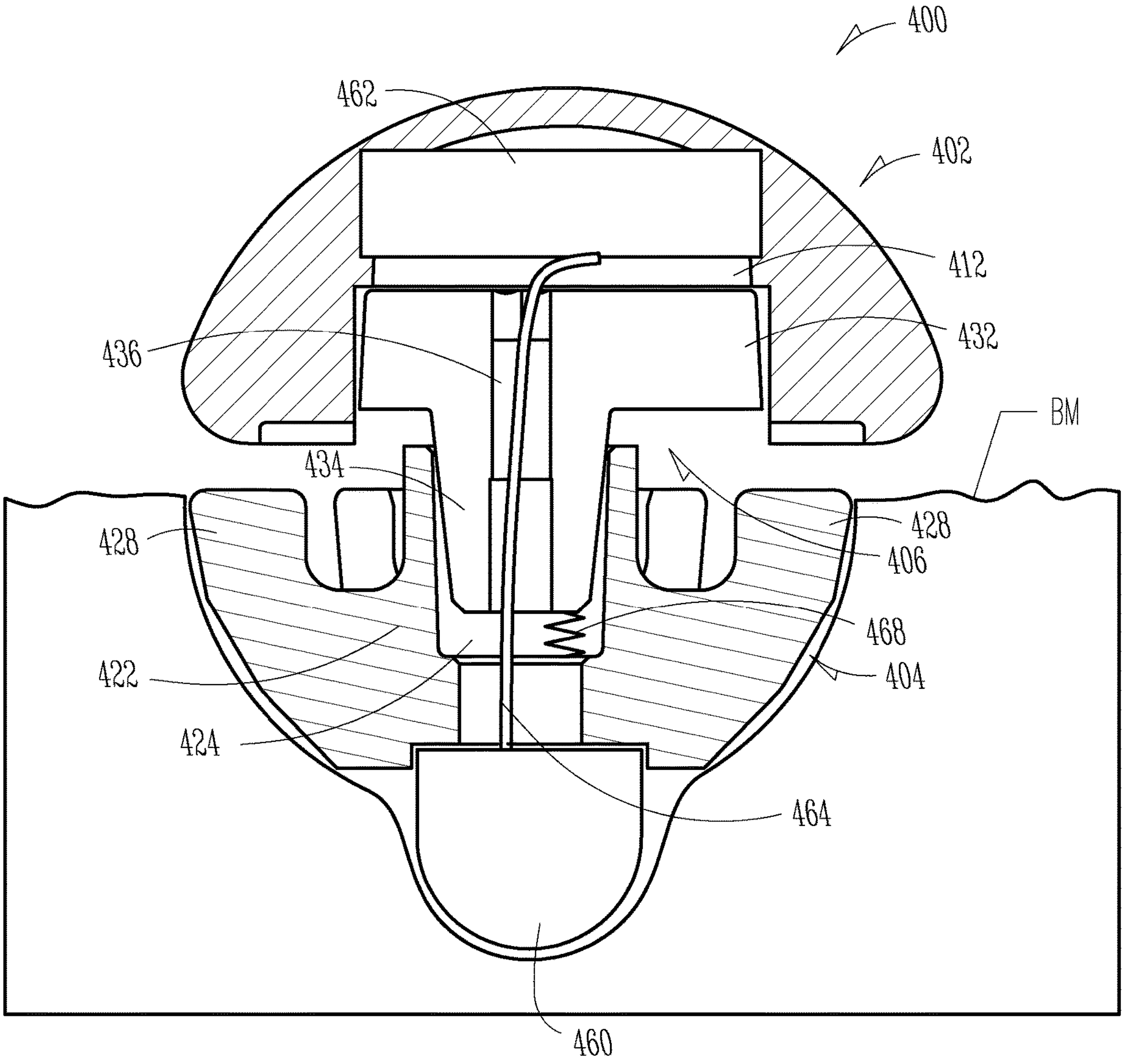
FIG. 7C is a third step of a process for assembling and implanting a sensor-enabled stemless humeral head implant of the present disclosure showing the adapter component positioned within a socket of the stemless anchor component and an electrical lead bunched up between the humeral head component and the stemless anchor component.

FIGS. 7A-7C illustrate an example method of assembling and implanting stemless humeral prosthesis 400 of the present disclosure. FIGS. 7A-7C illustrate an example method, but other sequences of steps can be used. Antenna module 460 and electronics module 462 are simplified in FIGS. 7A-7C, but can be constructed similarly as shown in FIG. 6.

FIG. 7A is a first step of a process for assembling stemless humeral prosthesis 400 of the present disclosure showing adapter component 406 positioned within socket 412 of prosthetic head component 402. Housing 480 of electronics module 462 can be fit into socket 412 of prosthetic head component 402. In examples, housing 480 can be press fit into socket 412 or upper chamber 414. In examples, prosthetic head component 402 can come in different sizes where bearing surface 410 has different radiuses. However, socket 412 within the different sizes of prosthetic head component 402 can remain the same to allow for assembly of housing 480 with each. In additional examples, housing 480 can be pre-assembled during a manufacturing process so that a user need not separately have to assemble electronics module 462 with prosthetic head component 402. Connector 466 can be inserted into the proximal end of passage 436 at driver socket 435 so that electrical lead 464 extends across the full length of adapter component 406. Plate 432 can have a taper and can be press fit into socket 412 to connect adapter component 406 to prosthetic head component 402.

FIG. 7B is a second step of a process for assembling stemless humeral prosthesis 400 of the present disclosure showing electrical lead 464 extended through adapter component 406 and coupled to stemless anchor component 404 at antenna module 460. Connector 466 (FIG. 7A) can be inserted into socket 474 FIG. 6). Stemless anchor component 404 can be inserted into bone matter BM. For example, projections 428 can be pressed into cancellous bone to fixate stemless anchor component 404 to bone matter BM. In examples, stemless anchor component 404 can be inserted into bone matter BM before connection to connector 466 and a tool can be used to insert connector 466 into extension 422 to facilitate coupling of connector 466 and socket 474 (FIG. 6). However, in other examples, adapter component 406 can be assembled with stemless anchor component 404 before inserting projections into bone.

FIG. 7C is a third step of a process for assembling stemless humeral prosthesis 400 of the present disclosure showing adapter component 406 positioned within socket 424 of stemless anchor component 404. The assembly of prosthetic head component 402 and adapter component 406 can be moved into proximity with stemless anchor component 404 so projection 434 can comprise a taper and can be inserted into socket 424. Electrical lead 464 can be flexed to fit within the space between prosthetic head component 402 and stemless anchor component 404, such as by being bunched up within passage 436.

Figure 8:
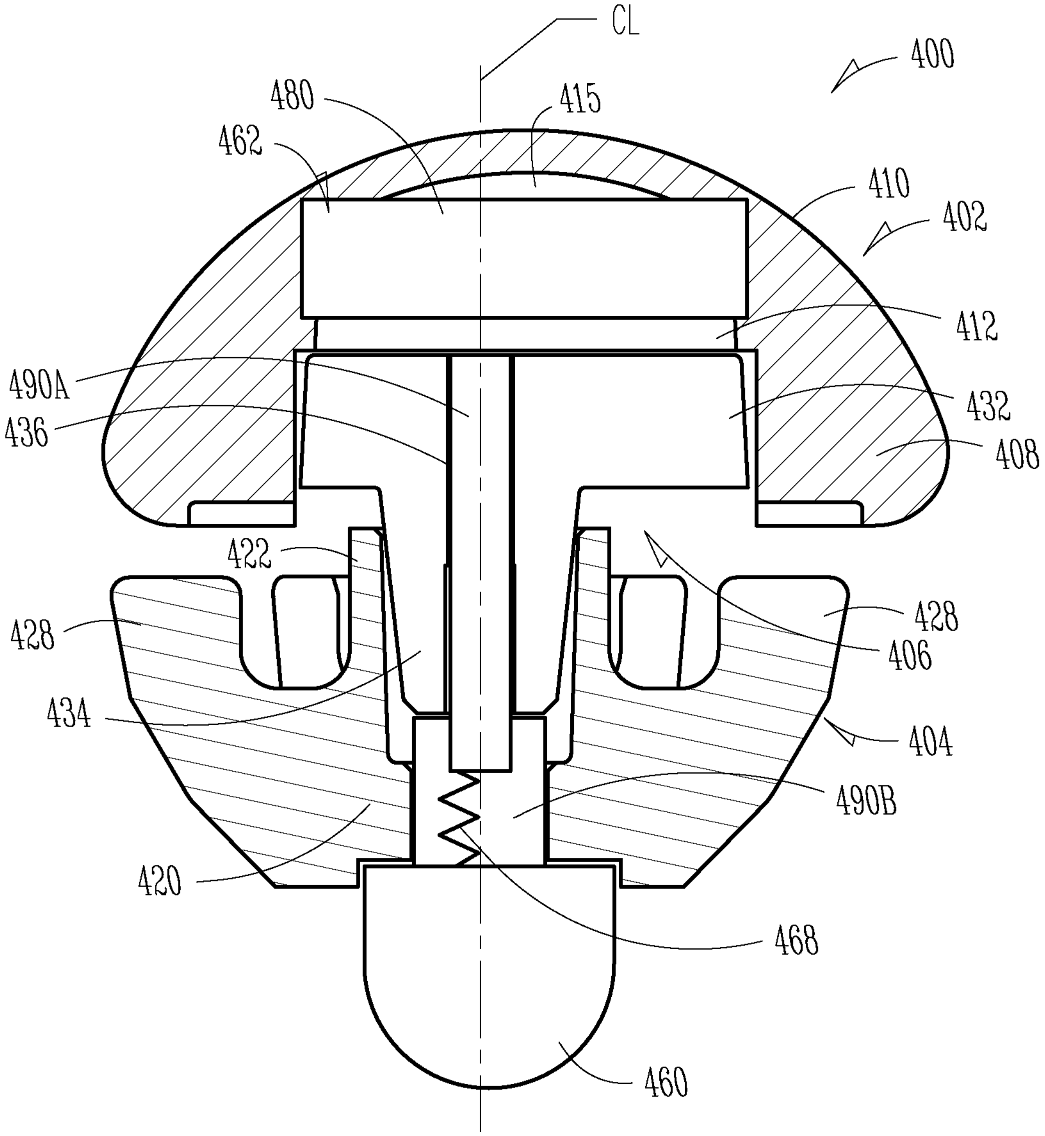
FIG. 8 a side cross-sectional view of an assembled sensor-enabled stemless humeral head implant having an antenna module and electronics module connected by rigid electrical leads.

FIG. 8 a side cross-sectional view of stemless humeral prosthesis 400 in an assembled state and having antenna module 460 and electronics module 462 connected by rigid electrical leads 490A and 490B. Stemless humeral prosthesis 400 of FIG. 8 can be the same as stemless humeral prosthesis 400 of FIG. 6 except that connector 466 and lead 464 can be replaced by electrical leads 490A and 490B. Electrical leads 490A and 490B can comprise components that can self-couple as adapter component 406 is mated with stemless anchor component 404, such as during the step illustrated in FIG. 7C. Electrical leads 490A and 490B, projection 434 and passage 436, extension 422 and socket 424 can all be configured to extend along centerline CL.

Electrical leads 490A and 490B can be formed from portions of housing 480 and antenna module 460, respectively. Similarly, all or some of the components of stemless humeral prosthesis 400 can be electrically conductive to allow electrical signals to be communicated through stemless humeral prosthesis 400, thereby reducing or eliminating the need for internal wiring. In additional examples, electrical leads 490A and 490B can be formed of material of adapter component 406 and stemless anchor component 404. Electrical leads 490A and 490B can include wires or the like to allow for electrical signals to be communicated between housing 480 and housing 470.

Figure 9:
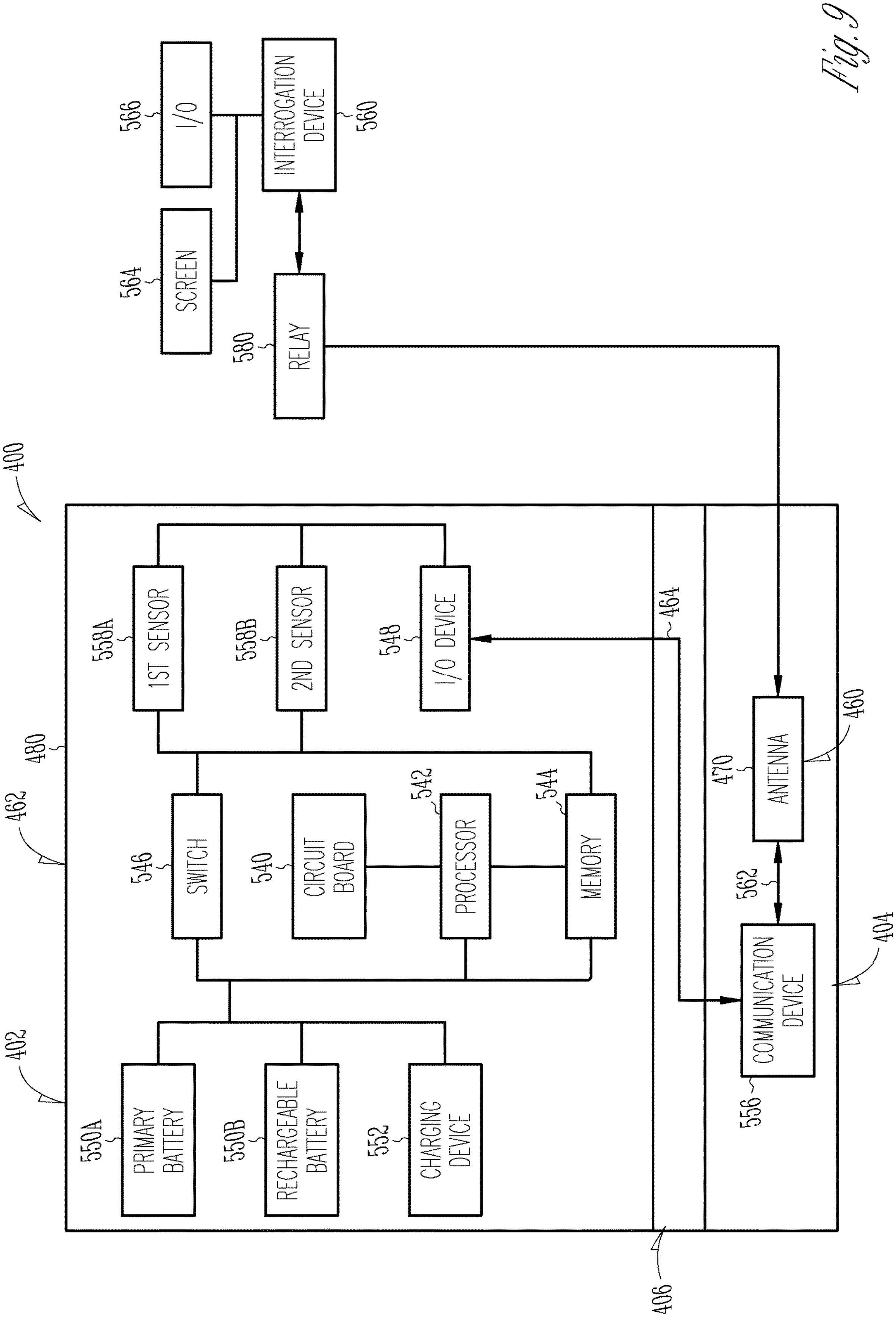
FIG. 9 is a schematic view of electronics elements used in the stemless humeral head prostheses of FIGS. 6-8 showing various sensors, communication devices and input and output devices.

FIG. 9 is a block diagram illustrating components of stemless humeral prosthesis 400, including electronics module 462 of prosthetic head component 402 and antenna module 460 of anchor component 404. Prosthetic head component 402 and anchor component 404 can be coupled by adapter component 406. Although described with reference to stemless humeral prosthesis 400, electronics module 462 can be configured for use with other orthopedic implant devices, such as prosthetic femoral components, prosthetic acetabular components, prosthetic humeral components and the like. Electronics module 462 can comprise housing 480, circuit board 540, processor 542, memory 544, switch 546, input/output (I/O) device 548, power source 550A, power source 550B, charging device 552, communication device 556, first sensor 558A and second sensor 558B. Housing 480 can be attached to or integral with prosthetic head component 402. Electronics module 462 can be in communication with interrogation device 560. Interrogation device 560 can comprise various electronics devices for powering electronics module 462 and obtaining information from electronics module 462, such as a mobile computing device (including via Bluetooth® connection), a base station, a dongle and other electronics devices. In examples, interrogation device 560 can be part of computing system 140 of FIG. 1A.

Housing 480 can comprise a structural component to hold and support other components of electronics module 462. Housing 480 can be integral with, attached to, or disposed inside of prosthetic head component 402. Housing 480 can be made of a medical grade plastic material, or can be made of other medical grade materials, such as stainless steel. Housing 480 can be made of a transparent or translucent material to facilitate transmission of light through housing 480 to improve visibility of any light sources disposed in or on housing 480. Housing 480 can be sealed to keep the components therein dry and away from engagement with the environment of electronics module 462.

Circuit board 540 can comprise a structural component for electrically and structurally coupling electrical components of electronics module 462. For example, circuit board 540 can comprise a silicon wafer or a chip onto which electrical couplings are attached for coupling switch 546, processor 542, memory 544, sensors 558A and 558B and the like.

Processor 542 can comprise an integrated circuit that controls operation of components of electronics module 462, such as I/O device 548, charging device 552, communication device 556 and sensors 558A and 558B. Processor can execute instructions stored in memory 544 to operate components of electronics module 462, such as charging device 552, and sensors 558A and 558B.

Memory 544 can comprise any suitable storage device, such as non-volatile memory, magnetic memory, flash memory, volatile memory, programmable read-only memory and the like. Memory 544 can include instructions stored therein for processor 542 to control operation of electronics module 462. For example, memory 544 can include instructions for operating I/O device 548, charging device 552, communication device 556 and sensors 558A and 558B, as well as coordinating output from electronics module 462. Memory 544 can additionally include reference data for comparing data from sensors 558A and 558B, such as threshold conditions or pressures for when prosthetic head component 402 (FIG. 5) are in kinematic alignment or when rechargeable power source 550B is charged or not charged.

Switch 546 can comprise a an on/off switch for providing power from power sources 550A and 550B to sensors 558A and 558B, etc. Switch 546 can comprise an “alternate action” switch when transitioning between open or closed states. In alternate action switches, a switch can be flipped for continuous “on” or “off” operation. Switch 546 can comprise a toggle switch, a knife switch, a relay or a push-button switch. In examples, electronics module 462 does not include a switch and electronics module 462 can be powered on so long as one of primary power source 550A and rechargeable power source 550B is at least partially charged.

I/O device 548 can comprise one or more devices for receiving input from and sending output to a user of electronics module 462. In order to operate or obtain information from electronics module 462. I/O device 548 can comprise a button, a knob, a dial and the like. In examples, I/O device 548 can be omitted and electronics module 462 can communicate with interrogation device 560 in order to operate electronics module 462.

I/O device 548 can comprise devices for providing visual and audio feedback. I/O device 548 can comprise a device for producing light waves, such as incandescent light bulbs, light-emitting-diodes and the like. In examples, I/O device 548 can be configured for emitting different colors or wavelengths of light. I/O device 548 can provide visual indications of when electronics module 462 is performing different functions, such as actively sensing. For example, I/O device 548 can be configured to emit orange, yellow and green light, so that an operator can confirm that different functions of electronics module 462 are being performed, or that a loss of communication or a malfunction of electronics module 462 is occurring.

I/O device 448 can include or comprise a device for making waves, such as a sound wave or a vibration wave. In an example, I/O device 448 can comprise an auditory device, such as a speaker or amplifier for producing an auditory signal or sound to indicate that electronics module 462 is in communication with interrogation device 560. In other examples, I/O device 548 can comprise tactile device, such as a reciprocating or oscillating device, for producing a vibration that can be felt by a surgeon, operator of interrogation device 560 or patient. For example, a wave can communicate with a device worn by a surgeon at interrogation device 560 that can vibrate when receiving the wave.

Communication device 556 can comprise one or more devices for receiving input from interrogation device 560 or providing an output to interrogation device 560 via various signals. Communication device 556 can provide signal 562 to interrogation device 560 via antenna module 460. Interrogation device 560 can thereafter, for example, display on human interface device 564, such as a video display monitor, an indication of information from electronics module 462. Interrogation device 560 can further comprise I/O device 566 to receiving input from and send output to a user of interrogation device 560, such as a surgeon. Communication device 556 is illustrated as being located within antenna module 460, but can alternately be located in housing 480.

Communication device 556 can receive signal 562 from interrogation device 560 via antenna module 460 for storing information on memory 544 or providing information to processor 542 for operating switch 546, charging device 552, sensors 558A and 558B, communication device 556, charging device 552 and other components of electronics module 462. In examples, communication device 556 can communicate using wireless communications signals, such as Bluetooth, WiFi, Zigbee, infrared (IR), near field communication (NFC), 3 GPP or other technologies. In examples, communication device 556 can comprise a wired connection or can include a port for receiving a wire for a wired connection. In examples, communication device 556 can communicate using one of more of the aforementioned IEEE 802.15.6-2012 protocol, an MICS protocol and an MBANs protocol.

Communication device 556 can optionally be used in conjunction with antenna relay 580 that extends outside of housing 480. Antenna relay 580 can comprise an independently implantable component that can be located within tissue between electronics module 462 and the skin. Antenna relay 580 can be uncoupled from each of electronics module 462 and the orthopedic implant. As such, antenna relay 580 can comprise an intermediary to allow native communication capabilities of communication device 556 to be enhanced or relayed outside of the patient with a stronger signal. Antenna relay 580 can be energized with power from interrogation device 560 to receive and rebroadcast a signal from electronics module 462.

Power source 550A can comprise an energy storage device such as a battery including an electrochemical cell, such as an alkaline or zinc-manganese battery. In examples, power source 550A can comprise a primary, or non-rechargeable battery.

In examples, one or both of power sources 550A and 550B can comprise one or more capacitors that can be charged by charging device 552, such as via an inductance signal, a magnetic signal or an RF energy signal. Thus, the capacitors can be charged by, for example, operation of an RF energy harvester, to provide a suitable amount of power to steadily operate electronics module 462 while the RF energy being harvested may fluctuate due to varying RF energy signal strength.

Power sources 550A and 550B can be configured to provide power to different components of electronics module 462. Primary battery, or power source 550A can provide long term battery power and can provide power to low-frequency sensor operations over the lifetime of electronics module 462. Rechargeable battery, or power source 550B can provide short term battery power and can provide short duration, high frequency sensor operations, such as during exercise conducted as part of post-operative rehabilitation. Electronics module 462 can include one or more of each of power sources 550A and 550B. Furthermore, in examples, electronics module 462 can exclude both of power sources 550A and 550B and can rely solely on power generated by an energy harvesting device. In examples, power sources 550A can comprise a capacitor and power source 550B can comprise an emergency or back-up power source, such as a non-rechargeable battery.

Charging device 552 can comprise one or more devices for providing power to power sources 550A and 550B. In examples, charging device 552 can comprise a coil that can be energized by an RF field. In examples, charging device 552 can comprise a coil that can be energized by a magnetic field. In examples, charging device 552 can comprise a magnetic loop antenna, such as a copper coil. In examples, charging device 552 can comprise one or more devices for converting radio frequency energy or waves into electricity. Examples of energy harvesting device are described in U.S. Pat. No. 9,021,277 to Shearer et al. (Powercast) titled "Powering Devices Using RF Energy Harvesting," which is incorporated herein by this reference. In examples, charging device 552 can comprise a lead or wire extending from housing 480 to a location remote therefrom. Such lead or wire can be positioned closer to the skin of the patent or can extend through the skin, e.g., be transdermal, of the patent to better connect to a charger or antenna relay 580. Such lead or wire can be placed during closing of the access site used to perform a surgical procedure, e.g., an arthroplasty. Such a lead or wire can be positioned away from metal and other components that can interfere with communication signals and can be unshrouded, e.g., not covered by a housing component, so to be more efficiently able to broadcast and/or receive radio signals. In additional examples, charging device 552 can be one or more components of the implanted device that can conduct electricity, such as prosthetic head component 402, adapter component 406 and stemless anchor component 404 (FIG. 6). Furthermore, charging device 552 can include a lead, such as a wire, that can be positioned close to the surface of the skin or protruding through the skin to facilitate charging, such as inductive charging. The lead itself can facilitate inductive charging or can be connected to an inductance charging component, such as a pad or coil to facilitate efficient transfer of energy. For example, a patient or technician can position an inductance charger in close proximity to a lead connected to charging device 552 to wirelessly charge the devices of the present disclosure.

Sensors 558A and 558B can comprise a variety of different sensors, such as temperature, pH, force, vibration, impact, position, motion, capacitance, conductance, impedance and the like. Only one of sensors 558A and 558B can be included in electronics module 462 or more than two sensors can be included in electronics module 462.

Electronics module 462 can be customized to include only the sensors and input and output devices that are desired for a particular procedure.

Figure 10A:
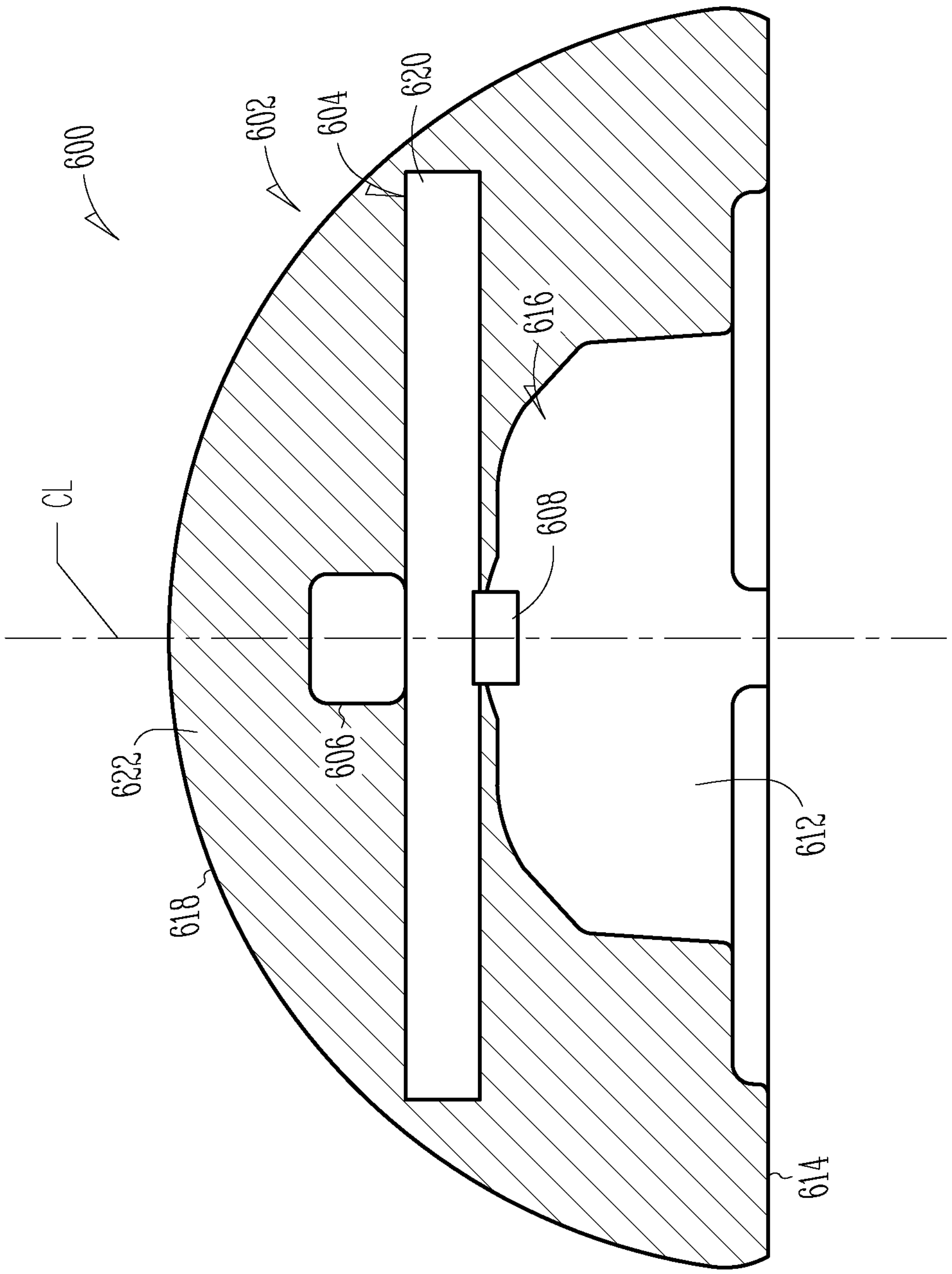
FIG. 10A is a side cross-sectional view of another example of a sensor-enabled humeral head implant comprising an electronics module having a sensor configured to sense contact between components of the implant.

FIG. 10A is a side cross-sectional view of sensor-enabled humeral head implant 600 comprising prosthetic head component 602, electronics module 604, antenna 606 and load cell 608. Prosthetic head component 602 can comprise adapter socket 612, proximal surface 614, upper chamber 616 and articulating surface 618.

Prosthetic head component 602 can comprise a component that forms a prosthetic humeral head as discussed herein. Articulating surface 618 can be configured to slide against a mating component, such as a bone socket including a glenoid or prosthetic acetabulum or a natural acetabulum. Proximal surface 614 can be configured to be brought close to or into contact with a resected bone surface of a humoral bone. An adapter, such as adapter component 630 of FIG. 10B or adapter component 406 of FIGS. 3-5, can be positioned within socket 612 and can extend into upper chamber 616. The adapter can be coupled to socket 612 via a Morse taper. Electronics module 604 can be positioned within prosthetic head component 602 to be in communication with upper chamber 616. In particular, electronics module 604 can be positioned within prosthetic head component 602 so that load cell 608 can extend into upper chamber 616. In additional example, load cell 608 can extend into socket 612. In examples, prosthetic head component 602 can include an additional pocket or chamber above upper chamber 616 to receive electronics module 604. The form factor of electronics module 604 can be configured to fit within a cavity inside prosthetic head component 602, such as between proximal surface 614 and articulating surface 618, to avoid changes to the shape of prosthetic head component. Electronics module 604 can be fit within prosthetic head component 602 during manufacturing so there are no extra intraoperative steps for a surgeon or technician to perform. Electronics module 604 can be retained within prosthetic head component 602 via press fit, adhesive, threaded engagement or other means. Electronics module 604 can comprise housing 620 in which electronics components are located. Antenna 606 and load cell 608 can be attached to or extend through housing 620. Electronics module 604 can be configured similarly as electronics module 462 to have housing 480 (FIGS. 6-8) disposed within prosthetic head component 602.

Electronics module 604 can include antenna 606 for communicating with other electronics modules or external communication devices, as described herein. In examples, antenna 60 can comprise a wire or coil of conducting material suitable for transmitting wireless signals. In examples, electronics module 604 can include antenna module 460 (FIG. 6) attached thereto or located remotely therefrom, such as via electrical lead 464. In examples, electronics module 604 can be configured similarly to electronics module 462 as depicted in FIG. 9, wherein one of sensors 558A and 558B comprise load cell 608 and antenna module 460 comprises antenna 606.

As can be seen in FIG. 10A, antenna 606 can be located against material 622 of prosthetic head component 602. In examples, antenna 606 can be completely surrounded by material 622 of prosthetic head component 602, but for the portion attached to electronics module 604. As such, it can be difficult for wireless communication signals, such as Bluetooth®, WiFi, Zigbee, infrared (IR), near field communication (NFC), 3GPP or other technologies, to pass through material 622 of humeral head. In the present disclosure, material 622 of prosthetic head component 602 can be fabricated of materials that allow wireless communication signals to pass therethrough. In examples, material 622 of prosthetic head component 602 can comprise material that improves transmission of wireless communication signals as compared to metallic materials. In examples, material 622 can comprise a pyrocarbon material and a ceramic material. In examples, material 622 of prosthetic head component 602 can comprise aluminum oxide ($Al_2O_3$). In examples, prosthetic head component 602 can comprise a composite of metal and ceramic components, as is described in U.S. Pat. No. 9,248,020 to Popoola et al., which is hereby incorporated herein by this reference. For example, a thin layer of metallic material can be used to provide structural support and facilitate communication of electronic communication signals, and ceramic layers can be added to the metallic layer to provide further strength without impeding wireless communication signals. In examples, material 622 of prosthetic head component 602 can be made partially (such as with a metallic or ceramic substrate) or completely of a polymer, such as polyethylene. As such, with the present disclosure, material 622 of humeral head 603 can be more capable of transmitting electronic and wireless communication signals, particularly as compared to humeral head prosthetic fabricated from all or primarily metallic materials. Because material 622 enables or enhances the ability to transmit wireless and electronic communication signals therethrough, prosthetic head component 602 can be configured to include electronics module 604 within the confines, space or envelope of existing prosthetic humeral head designs or can be allow prosthetic humeral head prosthesis to be designed without having to enlarge the desired shape or envelope of the design to specifically accommodate electronics components. As such, features like load cell 608 can be included within prosthetic head component 602 in convenient locations, such as to interact with anatomy or other components of humeral head implant 600.

Figure 10B:
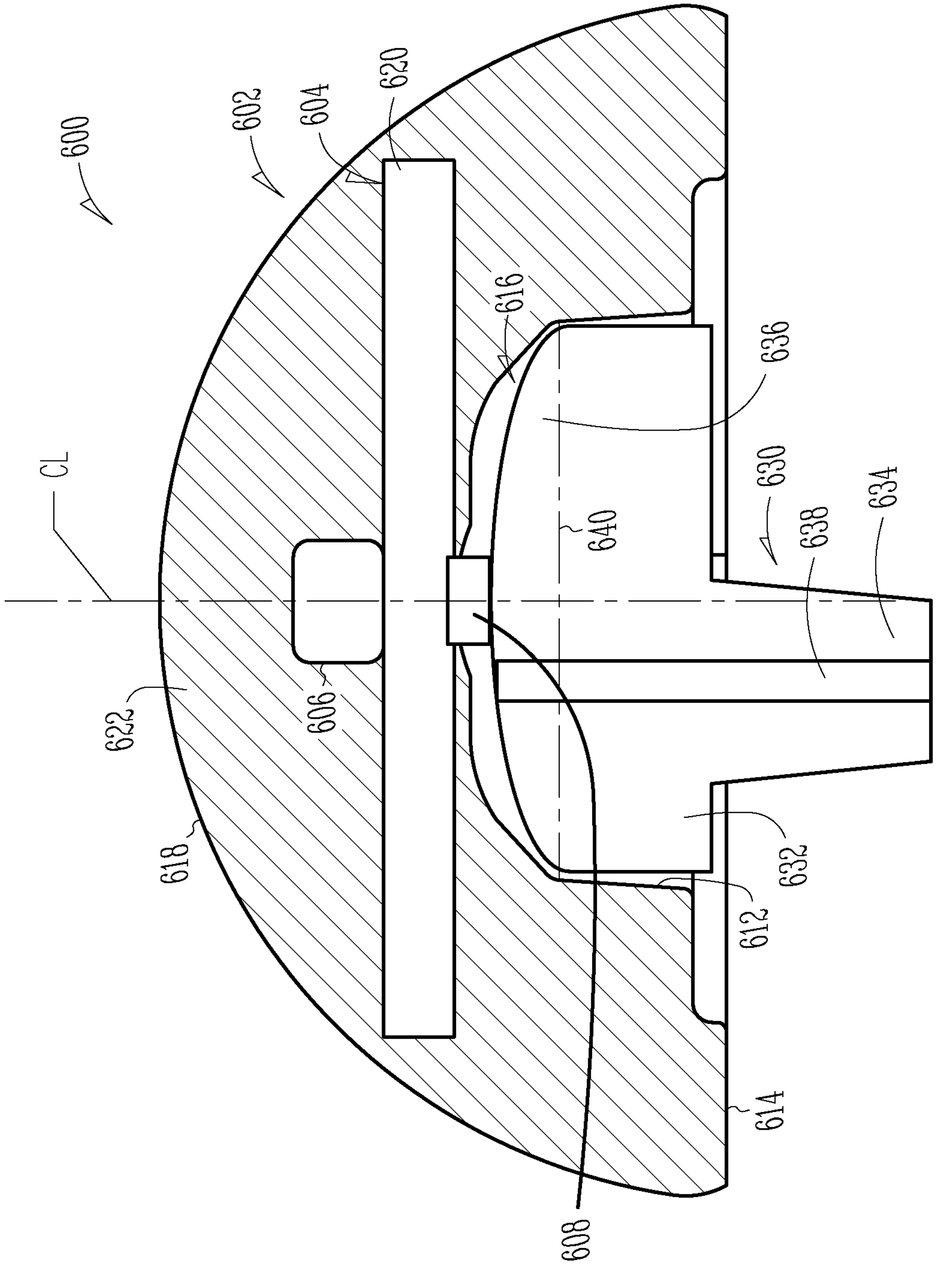
FIG. 10B is a side cross-sectional view of the sensor-enabled humeral head implant of FIG. 10A with an adapter component positioned within an adapter socket of a prosthetic humeral head component to engage the sensor.

FIG. 10B is a side cross-sectional view of sensor-enabled humeral head implant 600 of FIG. 10A with an adapter component 630 positioned within adapter socket 612 to engage load cell 608. Adapter component 630 can comprise plate 632, projection 634, dome 636 and passage 638. In examples, adapter component 630 can be configured similarly as adapter component 406 (FIGS. 6-8). Plate 632 can mate with socket 612, as mentioned, such as through a Morse taper. Projection 634 can extend proximally or downward from plate 632 to facilitate coupling with an anchor component as described herein. Passage 638 can extend through adapter component 630 to allow for the passage of wiring, tethers and communication lines, as described herein. In examples, passage 638 can be omitted. Dome 636 can extend distally or upward from plate 632 to penetrate into upper chamber 616. Dome 636 can be configured to engage with load cell 608. In examples, dome 636 can be omitted and load cell 608 can pass through upper chamber 616 to contact plate 632. Additionally, dome 636 can be replaced by projections or protrusions emanating from plate 632 to contact load cell 608. For example, adapter component 630 can comprise a cylindrical projection, a pyramid-shaped projection, a rectilinear-shaped projection and the like. In various examples, a portion of adapter component 630 can be configured to engage with load cell 608 in adapter socket 612 and/or upper chamber 616.

In examples, dome 636 can be configured to fully depress or partially depress load cell 608 to provide an indication of the position of adapter component 630 relative to prosthetic head component 602. Correspondingly, load cell 608 can be configured to provide an output signal having a magnitude or strength that corresponds to an amount or distance that load cell 608 is depressed, thereby allowing load cell 608 to provide a variable output. For example, dome 636 can project upward beyond horizontal plane 640 defining the juncture of socket 612 and upper chamber 616. In examples, load cell 608 can be positioned at the center of sensor-enabled humeral head implant 600 at center line CL. Similarly, the peak of dome 636 can be centered along center line CL. Thus, regardless of the relative rotation positions between adapter component 630 and prosthetic head component 602, dome will engage load cell 608. When adapter component 630 is fully or properly seated within socket 612, dome 636 can engage load cell 608 and fully depress load cell 608 to register a complete coupling between adapter component 630 and prosthetic head component 602. When adapter component 630 is partially or improperly seated within socket 612, dome 636 can partially engage load cell 608 and partially depress load cell 608 to register an incomplete coupling between adapter component 630 and prosthetic head component 602. For example, if adapter component 630 is inserted into socket 612 such that plate 632 is not parallel to plane 640, a portion of adapter component 630 may be fully seated while another portion of adapter component 630 would not be fully seated, thus partially depressing load cell 608, even though adapter component 630 would feel firmly in place to a surgeon. In an example, load cell 608 can register a signal of approximately 500 Newtons for a fully seated adapter component 630, which can proportionally decrease as adapter component 630 becomes less fully seated.

Load cell 608 can comprise a pressure sensor. Load cell 608 can comprise any suitable force or pressure sensors or readers, such as, but not limited to, piezoelectric sensors, force sensing resistors, force gauges, strain gauges, load cells, potentiometers, barometers, or the like. Example force sensors include force sensing resistor or capacitive flex circuits, piezoelectric film, piezoelectric elements, piezoresistive and piezoelectric polymers, metal foil strain gages, semiconductor strain gages, piezoresistive and capacitive pressure sensors, interferometric optical sensors, path displacement optical sensors, optical fiber force sensors, and other suitable sensing technologies. In other examples, load cell 608 can additionally or alternatively comprise a proximity sensor, a contact sensor, a gyroscope, an accelerometer, a motion sensor, an inertial measurement unit (IMU), and the like.

Load cell 608 can be used to provide pre-operative and intra-operative feedback regarding assembly of prosthetic head component 602 and adapter component 630 based on a sensed force or displacement of load cell 608 by adapter component 602. The feedback can also comprise an impaction force, acceleration data, and other sensor data that can be used, e.g., analyzed and evaluated, to determine implantation, impaction, proper seating and the like of prosthetic devices. The impaction force can be compared to threshold impaction force data stored in electronics module 604, a controller (e.g., interrogation device 560 (FIG. 9) or elsewhere that correlates displacement or force imparted to load cell 608 to proper seating or assembly of prosthetic head component 602 and adapter component 630. The feedback can also provide post-operative feedback to provide data relating to patient activity and use of sensor-enabled humeral head implant 600, such as via the use of accelerometers, inertial sensor or motion sensors.

Sensor-enabled humeral head implant 600 can include prosthetic head component 602 that has a cavity for the storage of a battery, electronics, sensors and an antenna. The battery can provide power to the sensors to enable collection of data for a number of years after implantation. The data collected by the sensors can be transmitted via the antenna to a base station near sensor-enabled humeral head implant 600 and uploaded to an application for users to view with a computing device. The sensors can comprise an inertial measurement unit (IMU) and a load cell. The load cell can be utilized intraoperatively to ensure the head is seated properly and monitor potential loosening of the head. The inertial measurement unit can be utilized postoperatively to collect range of motion data that could aid in relaying recovery progress and potential complications.

In a first example, sensor-enabled humeral head implant 600 can comprise antenna 606 and load cell 608 as illustrated in FIG. 10B, prosthetic head component can comprise ceramic material, and adapter component 630 can have passage 638 omitted. In a second example, sensor-enabled humeral head implant 600 can comprise load cell 608, antenna module 460 instead of antenna 606, adapter component 630 can include passage 638 for electrical lead 464, and humeral head implant 600 can comprise ceramic material, metallic material, or combinations thereof.

The systems, devices and methods discussed in the present application can be useful in providing implantable medical devices that have sensors to collect patient and implant data. The implantable medical devices can be appropriately sized and shaped without having to redesign existing medical device to accommodate electronics. The implantable medical devices described herein can be outfitted with electronics packages that can be separated into different modules or components that can be located within or mounted to the implantable medical devices in strategic places that take advantage of available internal space and external mounting locations. As such, the various modules and components can be located in places to improve performance while taking advantage of limited available space on the implantable medical device.

EXAMPLES

Example 1 is a humeral arthroplasty system including a sensor device, the humeral arthroplasty system comprising: a humeral head including a first portion of circuitry of the sensor device, the humeral head comprising an adapter socket; a taper adapter configured to seat within the adapter socket; a stemless humeral anchor couplable to the taper adapter; and a second portion of circuitry of the sensor device extending into the adapter socket.

In Example 2, the subject matter of Example 1 optionally includes wherein: the taper adapter and the stemless humeral anchor comprise a central bore extending therethrough; and the second portion of the circuitry of the sensor device is connected to the first portion by an electrical circuit extending through the taper adapter.

In Example 3, the subject matter of Example 2 optionally includes wherein the first portion of circuitry of the sensor device includes a power source.

In Example 4, the subject matter of Example 3 optionally includes wherein the first portion of circuitry further includes a sensor circuit.

In Example 5, the subject matter of any one or more of Examples 2-4 optionally include wherein the second portion includes an antenna or a wireless communication device.

In Example 6, the subject matter of Example 5 optionally includes wherein the second portion includes an additional sensor circuit.

In Example 7, the subject matter of any one or more of Examples 5-6 optionally include wherein the second portion further includes a communication circuit coupled to the antenna.

In Example 8, the subject matter of any one or more of Examples 2-7 optionally include wherein the electrical circuit extending through the taper adapter is an electrical lead.

In Example 9, the subject matter of Example 8 optionally includes wherein the electrical lead is a flexible wire hardwired into the first portion of circuitry of the sensor device.

In Example 10, the subject matter of Example 9 optionally includes wherein the electrical lead includes a connector on a first end opposite the first portion of circuitry of the sensor device.

In Example 11, the subject matter of Example 10 optionally includes wherein the electrical lead couples to the second portion of circuitry of the sensor device via the connector.

In Example 12, the subject matter of any one or more of Examples 2-11 optionally include wherein the electrical circuit extending through the taper adapter includes a first circuit pathway embedded in the humeral head, the taper adapter, and the stemless humeral anchor configured to conduct a first electrical signal between the first portion of circuitry and the second portion of circuitry.

In Example 13, the subject matter of Example 12 optionally includes wherein the electrical circuit extending through the taper adapter includes a second circuit pathway embedded in at least the taper adapter and configured to conduct a second electrical signal between the first portion of circuitry and the second portion of circuitry.

In Example 14, the subject matter of Example 13 optionally includes wherein the second electrical signal is a return path for the first electrical signal and the electrical circuit extending through the taper adapter is configured to transmit power from the first portion of circuitry to the second portion of circuitry.

In Example 15, the subject matter of any one or more of Examples 12-14 optionally include wherein the first circuit pathway is formed by first electrical conductors embedded in the taper adapter that electrically couple to second electrical conductors embedded in the stemless humeral anchor.

In Example 16, the subject matter of Example 15 optionally includes wherein the stemless humeral anchor completes the first circuit pathway with an internal electrical connection between the second electrical conductors and the second portion of circuitry.

In Example 17, the subject matter of any one or more of Examples 13-16 optionally include wherein the second circuit pathway includes a first conductive bias member electrically coupling the taper adapter and the first portion of circuitry and a second conductive bias member electrically coupling the taper adapter and the stemless humeral anchor.

In Example 18, the subject matter of any one or more of Examples 12-17 optionally include wherein one of the first portion of circuitry or the second portion of circuitry includes a measurement circuit configured to measure a parameter of the first circuit pathway correlated to an amount of impaction between the taper adapter and the humeral head or the taper adapter and the stemless humeral anchor.

In Example 19, the subject matter of Example 18 optionally includes comparing the amount of impaction is compared to a threshold impaction value indicating that the humeral head, the taper adapter and the stemless humeral anchor are assembled.

In Example 20, the subject matter of any one or more of Examples 18-19 optionally include comparing the amount of impaction is compared to a threshold impaction value indicating that the humeral head, the taper adapter and the stemless humeral anchor are assembled sufficient to withstand anticipated physiological loading.

In Example 21, the subject matter of any one or more of Examples 12-20 optionally include a glenoid prosthesis comprising a glenoid sensor, wherein the glenoid sensor is configured for communication with at least one of the first portion of circuitry and the second portion of circuitry.

In Example 22, the subject matter of any one or more of Examples 2-21 optionally include wherein the electrical circuit extending through the taper adapter comprises an electrical circuit through material of the taper adapter.

In Example 23, the subject matter of any one or more of Examples 1-22 optionally include wherein the humeral head comprises at least a portion that is fabricated from a ceramic material.

In Example 24, the subject matter of Example 23 optionally includes wherein the humeral head is fabricated entirely from ceramic material and the humeral head comprises a pocket to receive the first portion of circuitry.

In Example 25, the subject matter of any one or more of Examples 1-24 optionally include wherein: the second portion of circuitry of the sensor device comprises a force sensor extending into the adapter socket, wherein the taper adapter is configured to engage the force sensor when seated in the adapter socket.

In Example 26, the subject matter of Example 25 optionally includes wherein: the taper adapter is configured to fully depress the force sensor when the taper adapter is fully seated in the adapter socket; and the taper adapter is configured to partially depress the force sensor when the taper adapter is partially seater or misaligned within the adapter socket.

In Example 27, the subject matter of Example 26 optionally includes wherein: the force sensor is configured to generate a full signal when fully depressed; and the force sensor is configured to generate a partial signal when partially depressed.

Each of these non-limiting examples can stand on its own, or can be combined in various permutations or combinations with one or more of the other examples.

Various Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A humeral arthroplasty system including a sensor device, the humeral arthroplasty system comprising:

a humeral head including a first portion of circuitry of the sensor device, the first portion of circuitry including a sensor, the humeral head comprising an adapter socket;

a taper adapter configured to seat within the adapter socket;

a stemless humeral anchor couplable to the taper adapter; and a second portion of circuitry of the sensor device extending into the adapter socket, the second portion of circuitry including an antenna, wherein the second portion of circuitry is connected to the first portion of circuitry by an electrical circuit extending through the taper adapter.

2. The humeral arthroplasty system of claim 1, wherein:

the taper adapter and the stemless humeral anchor comprise a central bore extending therethrough.

3. The humeral arthroplasty system of claim 2, wherein the first portion of circuitry of the sensor device includes a power source.

4. The humeral arthroplasty system of claim 3, wherein the first portion of circuitry further includes a sensor circuit.

5. The humeral arthroplasty system of claim 2, wherein the second portion comprises a wireless communication device.

6. The humeral arthroplasty system of claim 1, wherein the second portion further includes a communication circuit coupled to the antenna.

7. The humeral arthroplasty system of claim 2, wherein the electrical circuit extending through the taper adapter is an electrical lead.

8. The humeral arthroplasty system of claim 7, wherein the electrical lead is a flexible wire hardwired into the first portion of circuitry of the sensor device.

9. The humeral arthroplasty system of claim 8, wherein the electrical lead includes a connector on a first end opposite the first portion of circuitry of the sensor device.

10. The humeral arthroplasty system of claim 9, wherein the electrical lead couples to the second portion of circuitry of the sensor device via the connector.

11. The humeral arthroplasty system of claim 2, wherein the electrical circuit extending through the taper adapter includes a first circuit pathway embedded in the humeral head, the taper adapter, and the stemless humeral anchor configured to conduct a first electrical signal between the first portion of circuitry and the second portion of circuitry.

12. The humeral arthroplasty system of claim 11, wherein the electrical circuit extending through the taper adapter includes a second circuit pathway embedded in at least the taper adapter and configured to conduct a second electrical signal between the first portion of circuitry and the second portion of circuitry.

13. The humeral arthroplasty system of claim 12, wherein the second electrical signal is a return path for the first electrical signal and the electrical circuit extending through the taper adapter is configured to transmit power from the first portion of circuitry to the second portion of circuitry.

14. The humeral arthroplasty system of claim 11, wherein the first circuit pathway is formed by first electrical conductors embedded in the taper adapter that electrically couple to second electrical conductors embedded in the stemless humeral anchor.

15. The humeral arthroplasty system of claim 14, wherein the stemless humeral anchor completes the first circuit pathway with an internal electrical connection between the second electrical conductors and the second portion of circuitry.

16. The humeral arthroplasty system of claim 12, wherein the second circuit pathway includes a first conductive bias member electrically coupling the taper adapter and the first portion of circuitry and a second conductive bias member electrically coupling the taper adapter and the stemless humeral anchor.

17. The humeral arthroplasty system of claim 11, wherein one of the first portion of circuitry or the second portion of circuitry includes a measurement circuit configured to measure a parameter of the first circuit pathway correlated to an amount of impaction between the taper adapter and the humeral head or the taper adapter and the stemless humeral anchor.

18. The humeral arthroplasty system of claim 17, further comprising comparing the amount of impaction to a threshold impaction value indicating that the humeral head, the taper adapter and the stemless humeral anchor are assembled.

19. The humeral arthroplasty system of claim 17, further comprising comparing the amount of impaction to a threshold impaction value indicating that the humeral head, the taper adapter and the stemless humeral anchor are assembled sufficient to withstand anticipated physiological loading.

20. The humeral arthroplasty system of claim 11, further comprising a glenoid prosthesis comprising a glenoid sensor, wherein the glenoid sensor is configured for communication with at least one of the first portion of circuitry and the second portion of circuitry.

21. The humeral arthroplasty system of claim 2, wherein the electrical circuit extending through the taper adapter comprises an electrical circuit through material of the taper adapter.

22. The humeral arthroplasty system of claim 1, wherein the humeral head is fabricated entirely from ceramic material and the humeral head comprises a pocket to receive the first portion of circuitry.

23. The humeral arthroplasty system of claim 1, wherein:

the second portion of circuitry of the sensor device further comprises a force sensor extending into the adapter socket, wherein the taper adapter is configured to engage the force sensor when seated in the adapter socket.

24. The humeral arthroplasty system of claim 23, wherein:

the taper adapter is configured to fully depress the force sensor when the taper adapter is fully seated in the adapter socket; and the taper adapter is configured to partially depress the force sensor when the taper adapter is partially seated or misaligned within the adapter socket.

25. The humeral arthroplasty system of claim 24, wherein:

the force sensor is configured to generate a full signal when fully depressed; and the force sensor is configured to generate a partial signal when partially depressed.

26. A humeral arthroplasty system comprising:

a humeral head comprising an adapter socket and a sensor device, the sensor device comprising a force sensor extending into the adapter socket; and a taper adapter configured to seat within the adapter socket and engage the force sensor, wherein the taper adapter is configured to fully depress the force sensor when the taper adapter is fully seated within the adapter socket, and wherein the taper adapter is configured to partially depress the force sensor when the taper adapter is partially seated or misaligned within the adapter socket;

wherein the force sensor is configured to generate a first signal when fully depressed and a second signal different from the first signal when partially depressed.

27. A humeral arthroplasty system including a sensor device, the humeral arthroplasty system comprising:

a humeral head including a first portion of circuitry of the sensor device, the humeral head comprising an adapter socket;

a taper adapter configured to seat within the adapter socket;

a stemless humeral anchor couplable to the taper adapter; and a second portion of circuitry of the sensor device, wherein the second portion of circuitry is electrically coupled to the first portion of circuitry by a first conductive bias member electrically coupling the taper adapter and the first portion of circuitry and a second conductive bias member electrically coupling the taper adapter and the stemless humeral anchor.

* * * * *